US012714714B2

(12) United States Patent
Sanchez

(10) Patent No.: US 12,714,714 B2
(45) Date of Patent: Aug. 25, 2026

(54) COMBINATION THERAPY FOR TREATING EXECUTIVE FUNCTION DISORDERS

(71) Applicant: Anaka Pharmaceuticals, Inc., Lexington, MA (US)

(72) Inventor: Hector Mario Sanchez, Santo Domingo (DO)

(73) Assignee: Anaka Pharmaceuticals, Inc., Lexington, MA (US)

( * ) Notice: Subject to any disclaimer, the term of this patent is extended or adjusted under 35 U.S.C. 154(b) by 472 days.

(21) Appl. No.: 18/275,354

(22) PCT Filed: Feb. 3, 2022

(86) PCT No.: PCT/EP2022/052587

§ 371 (c)(1),
(2) Date: Aug. 1, 2023

(87) PCT Pub. No.: WO2022/167527

PCT Pub. Date: Aug. 11, 2022

(65) Prior Publication Data

US 2024/0165124 A1 May 23, 2024

(30) Foreign Application Priority Data

Feb. 3, 2021 (GB) ..................................... 2101462

(51) Int. Cl.
*A61K 31/55* (2006.01)
*A61K 31/165* (2006.01)
*A61P 25/00* (2006.01)

(52) U.S. Cl.
CPC ............ *A61K 31/55* (2013.01); *A61K 31/165* (2013.01); *A61P 25/00* (2018.01)

(58) Field of Classification Search
CPC ........ A61K 31/165; A61K 31/55; A61P 25/00
See application file for complete search history.

(56) References Cited

U.S. PATENT DOCUMENTS

| | | | |
|---|---|---|---|
| 2011/0207718 | A1 | 8/2011 | Bird |
| 2019/0076415 | A1 | 3/2019 | During |
| 2019/0091179 | A1 | 3/2019 | Morrison et al. |

FOREIGN PATENT DOCUMENTS

| | | | |
|---|---|---|---|
| EP | 2505197 | 10/2012 | |
| EP | 3103444 | 12/2016 | |
| WO | 2010015029 | 2/2010 | |
| WO | 2013007698 | 1/2013 | |
| WO | WO-2018200844 A1 * | 11/2018 | ............. A61P 25/28 |
| WO | 2021023675 | 2/2021 | |

OTHER PUBLICATIONS

Novy et al. (2011) "Lacosamide neurotoxicity associated with concomitant use of sodium channel-blocking antiepileptic drugs: A pharmacodynamic interaction?" Epilepsy and Behavior, 20(1): 20-23.
Shandra et al. (2013) "Synergism of lacosamide with established antiepileptic drugs in the 6-Hz seizure model in mice" Epilepsia, 54(7):1167-1175.
Załuska-Ogryzek et al. (2021) "Interactions among Lacosamide and Second-Generation Antiepileptic Drugs in the Tonic-Clonic Seizure Model in Mice" Int. J. Mol. Sci., 22:5537, 17 pages.
Notice of Reasons for Refusal (English translation) dated Nov. 18, 2025, Application No. JP 2023-547057, 9 pages.

* cited by examiner

*Primary Examiner* — Sarah Pihonak
(74) *Attorney, Agent, or Firm* — Brian E. Davy; Bozicevic, Field & Francis LLP

(57) ABSTRACT

The present invention relates to the treatment of an executive function disorder, such as attention deficit hyperactivity disorder (ADHD) and/or autism with both lacosamide and oxcarbazepine.

18 Claims, No Drawings

COMBINATION THERAPY FOR TREATING EXECUTIVE FUNCTION DISORDERS

FIELD OF THE INVENTION

The present invention relates to the treatment of an executive function disorder, such as attention deficit hyperactivity disorder (ADHD) and/or autism with both lacosamide or a functionally equivalent analogue thereof and oxcarbazepine or a functionally equivalent analogue thereof.

BACKGROUND TO THE INVENTION

Executive function is a term that refers to mental control processes that enable physical, cognitive and/or emotional self-control and are necessary to maintain effective goal-directed behaviour. Deficits in executive function are associated with disorders, such as autism and attention deficit hyperactivity disorder (ADHD) ("Examining executive functioning in children with autism spectrum disorder, attention deficit hyperactivity disorder and typical development" Corbett et al., *Psychiatry Research* 166 (2009) 210-222).

Autism is a severe neurological disorder characterized by impairment in communication, reciprocal social interaction and a restricted range of activities and interests. The symptoms of autism fall on a continuum of severity known as autism spectrum disorder (ASD), which includes autistic disorder, Asperger syndrome and pervasive developmental disorder—otherwise not specified (PDD-NOS). Patients suffering from autism show deficits in many executive functions, including planning, cognitive flexibility, and working memory.

ADHD is a neurological disorder characterised by problems paying attention and difficulty controlling behaviour and impulsivity. Similarly to autistic patients, ADHD patients show deficits in many executive functions, including planning, working memory and flexibility ("Executive function and attention deficit hyperactivity disorder: stimulant medication and better executive function performance in children"; Kempton et al.; 1999, *Psychological medicine,* 29(3), 527-538).

Studies showed that a genetic linkage between ADHD and autism exists at chromosomal locations 2q24 and 16p13 ("A Genomewide Scan for Loci Involved in Attention-Deficit/Hyperactivity Disorder", Fisher et al. 2002, *Am. J. Hum. Genet.* 70, 1183-1196). In addition, various neuroscientific models have highlighted the common behavioural features, biological pathways and neuroanatomical correlates between autism and ADHD implicating the frontostriatal system including the frontal lobes and basal ganglia. These brain regions have been associated with deficits in executive function.

The underlying causes of ADHD and autism are not well understood. It has been hypothesized that they are related to deficiencies in dopamine production/firing and/or noradrenaline production/firing (e.g. "Binding of Dopamine D1 Receptor and Noradrenaline Transported in Individuals with Autism Spectrum Disorder: A PET Study", Kubota et al., 2020, *Cerebral Cortex,* 30: 6458-6468).

As a consequence, it is conventional in the art to treat ADHD and autism using molecular stimulants, such as methylphenidate (e.g. "Methylphenidate for children and adolescents with autism spectrum disorder."; Sturman et al., *Cochrane Database of Systematic Reviews* 11 (2017)). Molecular stimulants (such as methylphenidate) act by stimulating/modulating neurotransmitter release or recapture transporters in the brain. In the specific case of methylphenidate, this compound inhibits norepinephrine and dopamine reuptake by blocking both the norepinephrine transporter and dopamine transporter in brain cell membranes. This prevents dopamine clearance from synapses, elevating dopamine levels in the synapse and increasing dopamine signalling in the brain. However, the US Food and Drug Administration has now imposed a warning on methylphenidate packaging warning that this drug can cause addiction and the French Agence Nationale de Sécurité du Medicament has published a detailed report on the broad array of secondary symptoms caused by the medium to long term use of methylphenidate including insomnia, seizures, tic disorders, anxiety, irritability, aggressiveness, depression and mood swings ("Méthylphénidate: données d'utilisation et de sécurité d'emploi en France", Juillet 2013).

It has also been demonstrated that one third of the children who take methylphenidate develop symptoms of obsessive-compulsive behaviour ("Methylphenidate-induced obsessive-compulsive symptoms: A case report and review of literature"; Jhanda et al.; *J Pediatr Neurosci.* 2016; 11(4): 316-318). In addition, this drug may cause hallucinations, suicidal thoughts and psychotic behaviour that may result in aggressive and violent episodes. According to the U.S. Food and Drug Administration, it often leads to gastrointestinal problems and loss of appetite, endocrinology disorders that cause weight loss or other growth issues, cardiac events such as tachycardia, ventricular fibrillation and in some cases an implication in sudden death ("Weight, Height, and Body Mass Index in Patients with Attention-Deficit/Hyperactivity Disorder Treated with Methylphenidate", Diez-Suarez et al.; *J Child Adolesc Psychopharmacol.* 2017 Aug. 17).

Furthermore, the use of molecular stimulants is frequently associated with developing tolerance to the treatment, which, in turn, requires dose adjustment upward as treatment progresses. The data supports only a short-term efficacy of stimulants in treating executive function disorders, such as ADHD. A follow-up study after several years of molecular stimulant treatment showed that patients taking stimulant medications had the same level of symptoms as those who had never been medicate ("3-year follow-up of the NIMH MTA study". Jensen et al., 2007, *J. Am. Acad. Child Adolesc. Psychiatry.,* 46(8):989-1002).

Since the current strategies for treating executive function disorders, such as autism and ADHD utilize molecules that are not suitable for prolonged administration due to a high rate of side effects and developing tolerance to treatment, a need exists for a further treatments for executive function disorders.

SUMMARY OF THE INVENTION

In a first aspect, the present invention provides a combination or kit-of-parts of (a) lacosamide or a functionally equivalent analogue thereof and (b) oxcarbazepine or functionally equivalent analogue thereof for simultaneous, separate or sequential use in treating an executive function disorder.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a further aspect, the invention provides a kit, kit-of-parts, or system comprising (a) lacosamide or a functionally equivalent analogue thereof and (b) oxcarbazepine or a functionally equivalent analogue thereof.

In a further aspect, the invention provides a combination or kit-of-parts of (a) lacosamide or a functionally equivalent analogue thereof and (b) oxcarbazepine or a functionally equivalent analogue thereof for simultaneous, separate or sequential use in alleviating one or more symptoms of an executive function disorder.

Another aspect of the present invention provides a pharmaceutical composition comprising (a) lacosamide or a functionally equivalent analogue thereof and (b) oxcarbazepine or a functionally equivalent analogue thereof.

In a further aspect, the invention provides a method for treating an executive function disorder comprising administering (a) lacosamide or a functionally equivalent analogue thereof and (b) oxcarbazepine or a functionally equivalent analogue thereof to a subject suffering from an executive function disorder or symptoms thereof.

Another aspect of the present invention relates to lacosamide or a functionally equivalent analogue thereof for use in a method of treating an executive function disorder, wherein the method comprises administering (a) lacosamide or a functionally equivalent analogue thereof and (b) oxcarbazepine or a functionally equivalent analogue thereof to a subject suffering from the executive function disorder, preferably wherein the administration is sequential, simultaneous or separate.

In a further aspect, the invention provides oxcarbazepine or a functionally equivalent analogue thereof for use in a method of treating an executive function disorder, wherein the method comprises administering (a) oxcarbazepine or a functionally equivalent analogue thereof and (b) lacosamide or a functionally equivalent analogue thereof to a subject suffering from the executive function disorder, preferably wherein the administration is sequential, simultaneous or separate.

In a further aspect, the invention provides the use of (a) lacosamide or a functionally equivalent analogue thereof and (b) oxcarbazepine or a functionally equivalent analogue thereof in the manufacture of a medicament for the treatment of an executive function disorder. The medicament may, for example, be a sequentially administrable medicament, or a co-administrable medicament.

Also provided is a combination or kit-of-parts of (a) lacosamide or a functionally equivalent analogue thereof and (b) oxcarbazepine or a functionally equivalent analogue thereof for simultaneous, separate or sequential use in therapy.

Also provided is oxcarbazepine or a functionally equivalent analogue thereof for use in a method of treating an executive function disorder.

Other preferred embodiments of the uses, methods, kits, systems, kits-of-parts and compositions according to the invention appear throughout the specification and in particular in the examples.

The present inventor has surprisingly discovered that a combination of lacosamide (or functionally equivalent analogue thereof) and oxcarbazepine (or functionally equivalent analogue thereof) can effectively treat and manage executive dysfunction symptoms in a subject suffering from an executive function disorder, such as ADHD or autism.

As illustrated by the Examples, treatment with a combination of lacosamide (or functionally equivalent analogue thereof) and oxcarbazepine (or functionally equivalent analogue thereof) may advantageously show no (or little) evidence of unwanted side effects and/or developing tolerance upon prolonged administration of the treatment.

Surprisingly, the effects of the combination of lacosamide (or functionally equivalent analogue thereof) and oxcarbazepine (or functionally equivalent analogue thereof) on alleviating symptoms of executive functions disorders far exceed the effects observed upon administration of lacosamide monotherapy or oxcarbazepine monotherapy. In addition, the dose of lacosamide in the combination therapy may be substantially lower than in lacosamide monotherapy, which may reduce the chances of exhibiting any unwanted side effects.

Without wishing to be bound by theory, it is thought that the combination of lacosamide (or functionally equivalent analogue thereof) and oxcarbazepine (or functionally equivalent analogue thereof) tends to show the advantageous effects discussed above through improving ionic regulation of sodium and/or potassium.

DETAILED DESCRIPTION OF THE INVENTION

Stimulants such as methylphenidate may appear to quickly control one or more of the symptoms of executive function disorder, however they only treat the symptoms in the short-term without addressing the underlying etiology. Such stimulants do not therefore provide a suitable long-term treatment solution.

The present inventor has now surprisingly discovered that certain compounds which are active in the brain but which do not stimulate neurotransmitter release or recapture transporters in the brain can be used to treat an executive function disorder, such as autism or ADHD. This "non-stimulant" approach provides a progressive and long-lasting stabilisation of the symptoms of the executive function disorder. This is indicative that these compounds functionally address the etiological source of the disorder.

For example, this approach may result in one or more or all of the following:

(i) an improvement of cognitive function;
(ii) an improvement of cognitive performance;
(iii) a reduction in hyperactivity and/or impulsivity;
(iv) a reduction in involuntary enuresis;
(v) an improvement in the sleep quality;
(vi) an improvement in social skills;
(vii) an improvement in mood;
(viii) decreased anhedonia;
(ix) decreased tachypsichia;
(x) regulation of dysphoria; and/or
(xi) a reduction in stereotypies.

"Non-stimulant" compounds are known in the art to treat conditions such as epilepsy and bipolar disorder. An exemplary compound is lacosamide. Lacosamide's chemical name is (2R)-2-(acetylamino)-N-benzyl-3-methoxypropanamide and it has the following structure:

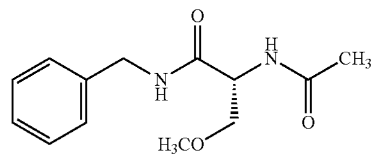 [SMILES: COC[C@@H](NC(C)=O)C(=O)NCc1ccccc1]

Lacosamide is a well-known anticonvulsant compound approved for the adjunctive treatment of partial-onset seizures and neuropathic pain.

Lacosamide is a functionalized amino acid that is believed to act through voltage-gated sodium channels ("Current understanding of the mechanism of action of the antiepileptic drug lacosamide" Rogawski et al., 2015, *Epilepsy Research,* 110: 189-205). Lacosamide enhances the slow inactivation of voltage-gated sodium channels without affecting the fast inactivation of voltage-gated sodium channels. This inactivation prevents the channel from opening, helping end the action potential. Lacosamide slows the recovery from inactivation and hence reduce the ability of neurons to fire action potentials. Inactivation only occurs in neurons firing action potentials; this means that drugs that modulate fast inactivation selectively reduce the firing in active cells. Slow inactivation is similar but does not produce complete blockade of voltage gated sodium channels, with both activation and inactivation occurring over hundreds of milliseconds or more. Lacosamide makes this inactivation happen at less depolarized membrane potentials. This means that lacosamide only affects neurons which are depolarized or active for long periods of time, typical of neurons at the focus of epilepsy ("The investigational anticonvulsant lacosamide selectively enhances slow inactivation of voltage-gated sodium channels" Errington et al., 2008, *Molecular Pharmacology,* 73(1): 157-69). Lacosamide administration results in the inhibition of repetitive neuronal firing, the stabilization of hyperexcitable neuronal membranes, and the reduction of long-term channel availability, but does not affect physiological function ("Development of lacosamide for the treatment of partial-onset seizures" Doty et al., 2013, *Ann N Y Acad Sci.* 1291: 56-68). Lacosamide does not affect α-amino-3-hydroxy-5-methyl-4-isoxazolepropionic acid (AMPA), kainate, N-methyl-D-aspartate (NMDA), $GABA_A$, $GABA_B$ or a variety of dopaminergic, serotonergic, adrenergic, muscarinic or cannabinoid receptors and does not block potassium or calcium currents ("Seeking a mechanism of action for the novel anticonvulsant lacosamide" Errington et al., 2006, *Neuropharmacology,* 50(8): 1016-29). Lacosamide does not modulate the reuptake of neurotransmitters including norepinephrine, dopamine, and serotonin ("Lacosamide: a review of preclinical properties" Beyreuther et al., 2007, *CNS Drug Reviews,* 13 (1): 21-42). In addition, it does not inhibit GABA transaminase.

A further exemplary compound of "non-stimulant" compounds is oxcarbazepine. Oxcarbazepine's chemical name is 5-oxo-6H-benzo[b][1]benzazepine-11-carboxamide and it has the following structure:

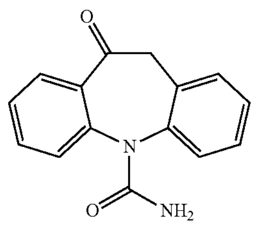 [SMILES: NC(=O)N1c2ccccc2CC(=O)c2ccccc21]

Oxcarbazepine is an anticonvulsant used to reduce the occurrence of epileptic episodes and to treat focal (partial) seizures.

Oxcarbazepine is a prodrug, which is largely metabolized to its pharmacologically active 10-monohydroxy derivative licarbazepine (sometimes abbreviated MHD). Oxcarbazepine and MHD exert their action by blocking voltage-sensitive sodium channels, thus leading to the stabilization of hyper-excited neural membranes, suppression of repetitive neuronal firing and diminishment propagation of synaptic impulses. Anticonvulsant effects of oxcarbazepine could be attributed to enhanced potassium conductance and modulation of high-voltage activated calcium channels.

Importantly, the present inventor has surprisingly discovered that a combination of lacosamide (or functionally equivalent analogue thereof) and oxcarbazepine (or functionally equivalent analogue thereof) can effectively treat and manage executive dysfunction symptoms in a subject suffering from an executive function disorder, such as ADHD and/or autism. The effects of the combination of non-stimulant compounds such as lacosamide and oxcarbazepine on alleviating symptoms of executive functions disorders far exceed the effects observed upon administration of lacosamide monotherapy or oxcarbazepine monotherapy.

Thus, the present invention provides a combination or kit-of-parts of (a) lacosamide or a functionally equivalent analogue thereof and (b) oxcarbazepine or a functionally equivalent analogue thereof for simultaneous, separate or sequential use in treating an executive function disorder. Preferably, the present invention provides a combination or kit-of-parts of (a) lacosamide and (b) oxcarbazepine for simultaneous, separate or sequential use in treating an executive function disorder.

Also contemplated are analogues of lacosamide, wherein the analogues are functionally equivalent to lacosamide. The analogues may have significant structural similarity to the structure of lacosamide. By "functionally equivalent" analogue of lacosamide is meant that the analogue is a non-stimulant and/or has a therapeutic effect on patients suffering from executive function disorder that is equivalent to that of lacosamide. The analogue may, for example, be the S enantiomer, (S)-2-(acetylamino)-N-benzyl-3-methoxypropanamide; a racemic mixture of the R enantiomer and the S enantiomer; or rufinamide. Rufinamide's chemical name is 1-[(2,6-difluorophenyl)methyl]-1H-1,2,3-triazole-4 carboxamide (marketed under brand name BANZEL™ or Inovelon™). Thus, in a preferred embodiment, the analogue that is functionally equivalent to lacosamide is the S and R racemate of lacosamide, or rufinamide.

Also contemplated are analogues of oxcarbazepine, wherein the analogues are functionally equivalent to oxcarbazepine. The analogues may have significant structural similarity to the structure of oxcarbazepine and may preferably be a metabolite of oxcarbazepine. By "functionally equivalent" analogue of oxcarbazepine is meant that the analogue is a non-stimulant and/or has a therapeutic effect on patients suffering from executive function disorder that is equivalent to that of oxcarbazepine. The analogue may, for example, be (L- and/or R-) licarbazepine (also known as 10-monohydroxy derivative (MHD)), eslicarbazepine and eslicarbazepine acetate. Thus, in a preferred embodiment, the analogue that is functionally equivalent to oxcarbazepine is (L- and/or R-) licarbazepine, eslicarbazepine or eslicarbazepine acetate.

The executive function disorder may preferably be ADHD and/or autism. For example, the subject may suffer from both ADHD and autism, and the treatment may be administered to such a subject to treat both of these disorders. Alternatively, the subject may suffer from ADHD and optionally not suffer from any further executive function disorder. Alternatively, the subject may suffer from autism and optionally not suffer from any further executive function disorder.

The term "autism" as used herein is intended to encompass autism spectrum disorder (ASD), which includes autistic disorder, Asperger syndrome and pervasive developmental disorder—otherwise not specified (PDD-NOS). Thus, in some embodiments, the executive function disorder is autism and may, for example, be selected from autistic disorder, Asperger syndrome and pervasive developmental disorder—otherwise not specified (PDD-NOS).

The term "ADHD" as used herein is intended to encompass all ADHD sub-types, including:

(i) ADHD predominantly inattentive type (ADHD-PI or ADHD-I) presents with symptoms including being easily distracted, forgetful, daydreaming, disorganization, poor concentration, and difficulty completing tasks;

(ii) ADHD, predominantly hyperactive-impulsive type (ADHD-PH or ADHD-HI) presents with excessive fidgetiness and restlessness, hyperactivity, difficulty waiting and remaining seated and immature behaviour; destructive behaviours may also be present; and (iii) ADHD, combined type (ADHD-C) which is a combination of subtypes (i) and (ii) above.

ADHD predominantly inattentive type (ADHD-PI or ADHD-I) lacks a hyperactivity component and may also be known as Attention Deficit Disorder (ADD).

In some embodiments, the executive function disorder is ADHD and may, for example, be selected from ADHD-PI, ADHD-PH and/or ADD.

As shown in the Examples, treatment of subjects suffering from an executive function disorder such as ADHD and/or autism with lacosamide and oxcarbazepine eliminated, alleviated or ameliorated certain symptoms of these executive function disorders. For example, hyperactivity and/or impulsivity was reduced, social interaction was improved, involuntary enuresis was eliminated, and sleep activity was improved.

It will be appreciated that the treatment of the executive function disorder, such as autism and/or ADHD, may result in the elimination, alleviation or amelioration of one or more symptoms of these executive function disorders and need not necessarily alleviate or ameliorate every symptom of the executive function disorder that the patient experienced prior to treatment.

By 'elimination' of a symptom is meant that the subject essentially no longer experiences that symptom. By 'alleviation' of a symptom is meant that the subject experiences a significant improvement in the symptom. The alleviation is preferably from severe to mild. By 'amelioration' of a symptom is meant that the subject experiences a modest improvement in the symptom.

Thus, in particular embodiments, the treatment, use and the like provided herein may result in the elimination, alleviation or amelioration of one or more symptoms of the executive function disorder. For example, one or more symptoms may be alleviated and one or more different symptoms may be ameliorated. One or more of the following, or one or more symptoms within these categories, may be eliminated, alleviated or ameliorated:

(i) hyperactivity and/or impulsivity;
(ii) involuntary enuresis;
(iii) aggressive behaviour;
(iv) insomnia or hypersomnia;
(v) impaired attention processing;
(vi) impaired communication;
(vii) impaired social skills;
(viii) impaired visual and/or auditory processing;
(ix) anhedonia;
(x) tachypsichia;
(xi) dysphoria; and/or
(xii) stereotypies.

Thus, the treatment may result in one or more or all of the following:

(i) an improvement of cognitive function;
(ii) an improvement of cognitive performance;
(iii) a reduction in hyperactivity and/or impulsivity;
(iv) a reduction in involuntary enuresis;
(v) an improvement in the sleep quality;
(vi) improved social skill and communication;
(vii) an improvement in mood;
(viii) decreased anhedonia;
(ix) decreased tachypsichia;
(x) regulation of dysphoria; and/or
(xi) a reduction in stereotypies.

Thus, the invention provides a method for treating an executive function disorder comprising administering (a) lacosamide or a functionally equivalent analogue thereof and (b) oxcarbazepine or functionally equivalent analogue thereof to a subject suffering from an executive function disorder or symptoms thereof. Preferably, the executive function disorder is ADHD and/or autism. Preferably, the method comprises administering (a) lacosamide and (b) oxcarbazepine, which administration may be simultaneous, sequential or separate.

In some embodiments, according to all aspects of the invention, the amount of lacosamide (or a functionally equivalent analogue thereof) and oxcarbazepine (or functionally equivalent analogue thereof) administered to the subject is a therapeutically effective amount.

As used herein, the phrase "a therapeutically effective amount", or "a clinically effective dose" means an amount of lacosamide (or a functionally equivalent analogue thereof) and oxcarbazepine (or functionally equivalent analogue thereof) that, when administered to a subject for treating an executive function disorder, such as autism or ADHD, is sufficient to effect such treatment of the executive function disorder. This amount will vary depending, for instance, on factors such as the specific agent used, the severity of subject's symptoms, the age, weight and relative health of the subject and the route and form of administration. Determining the relevant therapeutically/clinically effective amount for a specific subject based on such factors is routine for the person skilled in the art (e.g. an attending medical practitioner) once provided with the teaching of the present invention. Treatment of an executive function disorder as described herein should be understood to mean an improvement in one of more of the symptoms. This may include, for instance, an improvement in focus, concentration, sleep quality, cognitive function, cognitive performance, mood, communication skills and/or memory, being more organised, being more socially active and/or being able to complete tasks more easily. It may also include a reduction in hyperactivity, impulsivity, involuntary enuresis, fidgetiness and/or restlessness and/or a reduction in immature and/or destructive behaviours. It will be understood by the skilled person that the treatment generally refers to an improvement in one or more of the symptoms as described, typically a progressive and long-lasting improvement.

In a further aspect, the present invention provides lacosamide or a functionally equivalent analogue thereof for use in a method of treating an executive function disorder, wherein the method comprises administering (a) lacosamide or a functionally equivalent analogue thereof and (b) oxcarbazepine or functionally equivalent analogue thereof to a subject suffering from the executive function disorder, preferably wherein the administration is sequential, simultaneous or separate. Preferably, the executive function disorder is ADHD and/or autism. Preferably, the method comprises administering (a) lacosamide and (b) oxcarbazepine to the subject, which administration may be simultaneous, sequential or separate. Preferably, the amount of lacosamide (or a functionally equivalent analogue thereof) and oxcarbazepine (or functionally equivalent analogue thereof) administered to the subject is a therapeutically effective amount.

In a further aspect, the invention provides oxcarbazepine or functionally equivalent analogue thereof for use in a method of treating an executive function disorder, wherein the method comprises administering (a) oxcarbazepine or functionally equivalent analogue thereof and (b) lacosamide or a functionally equivalent analogue thereof to a subject suffering from the executive function disorder, preferably wherein the administration is sequential, simultaneous or separate. Preferably, the executive function disorder is ADHD and/or autism. Preferably, the method comprises administering (a) lacosamide and (b) oxcarbazepine to the subject, which administration may be simultaneous, sequential or separate. Preferably, the amount of lacosamide (or a functionally equivalent analogue thereof) and oxcarbazepine (or functionally equivalent analogue thereof) administered to the subject is a therapeutically effective amount.

More particularly, one or more of the following may be eliminated, alleviated or ameliorated: overabundant thought; sudden disconnections; distressing thoughts; mood swings; hypomania or hypersomnia; aggressive behaviour; involuntary enuresis, impaired attention processing; impaired communication; lethargy; tiredness; impaired non-verbal reasoning; deficient social skills; anhedonia; tachypsichia; dysphoria; and/or stereotypies.

Thus, alternatively viewed, provided is a method of eliminating, alleviating and/or ameliorating one or more of the above symptoms by administering a combination of lacosamide (or functionally equivalent analogue thereof) and oxcarbazepine (or functionally equivalent analogue thereof) to a subject in need thereof. Preferably, the subject suffers from executive function disorder. More preferably still, the subject suffers from ADHD and/or autism. Preferably, the method comprises administering a combination of lacosamide and oxcarbazepine, which administration may be simultaneous, sequential or separate. Preferably, the amount of lacosamide (or a functionally equivalent analogue thereof) and oxcarbazepine (or functionally equivalent analogue thereof) administered to the subject is a therapeutically effective amount.

In some embodiments, according to all aspects of the invention, the dose of lacosamide, especially in paediatric patients, may be in the range of about 1-12 milligrams of the agent per kilogram body weight of the subject per day (mg/kg/day). In specific embodiments, the amount may be at least or about 1 mg/kg/day, at least or about 2 mg/kg/day, at least or about 4 mg/kg/day, at least or about 6 mg/kg/day, at least or about 8 mg/kg/day, or at least or about 10 mg/kg/day. In further embodiments, the amount may be in the range of about 2-6 mg/kg/day, 1-10 mg/kg/day or 1-15 mg/kg/day.

In some embodiments, according to all aspects of the invention, the dose of oxcarbazepine, especially in paediatric patients, may be in the range of about 1-60 milligrams of the agent per kilogram body weight of the subject per day (mg/kg/day).

Typically, the treatment according to the invention is administered only for the treatment of an executive function disorder. Preferably, the executive function disorder is associated with the deficits in the frontostriatal system including the frontal lobes and basal ganglia of the brain.

More preferably still, the treatment according to the invention is administered only for the treatment of autism and/or ADHD, or for the treatment of one or more symptoms of autism and/or ADHD.

Thus, in some embodiments, according to all aspects of the invention, the treatment is of a subject suffering from the executive function disorder, such as autism and/or ADHD, who does not suffer from one or more or any of the following disorders; and/or the treatment according to the invention is not administered for the treatment of one or more or any of the following disorders: epilepsy, bipolar disorder, seizures, neuropathic pain, depression, anxiety, schizophrenia, obsessive-compulsive disorder (OCD), Alzheimer's disease, Parkinson's disease, corticobasal degeneration, progressive supranuclear palsy, chronic traumatic encephalopathy, multiple system atrophy, amyotrophic lateral sclerosis, vascular cognitive impairment, ischemic stroke, frontotemporal dementia, Lewy body dementia, Tourette's syndrome and/or traumatic injuries to the brain, preferably epilepsy. For example, the treatment may be of a subject suffering from autism who does not suffer from one or more or any of the following disorders: epilepsy, bipolar disorder, seizures, neuropathic pain, depression, anxiety, schizophrenia, obsessive-compulsive disorder (OCD), Alzheimer's disease, Parkinson's disease, corticobasal degeneration, progressive supranuclear palsy, chronic traumatic encephalopathy, multiple system atrophy, amyotrophic lateral sclerosis, vascular cognitive impairment, ischemic stroke, frontotemporal dementia, Lewy body dementia, Tourette's syndrome and/or traumatic injuries to the brain, preferably epilepsy. As another example, the treatment may be of a subject suffering from ADHD who does not suffer from one or more or any of the following disorders: epilepsy, bipolar disorder, seizures, neuropathic pain, depression, anxiety, schizophrenia, obsessive-compulsive disorder (OCD), Alzheimer's disease, Parkinson's disease, corticobasal degeneration, progressive supranuclear palsy, chronic traumatic encephalopathy, multiple system atrophy, amyotrophic lateral sclerosis, vascular cognitive impairment, ischemic stroke, frontotemporal dementia, Lewy body dementia, Tourette's syndrome and/or traumatic injuries to the brain, preferably epilepsy.

In some embodiments, according to all aspects of the invention, the subject may previously have received lacosamide (or functionally equivalent analogue thereof) therapy (without oxcarbazepine), for example lacosamide monotherapy, for example to treat an executive function disorder, which may be the same or a different an executive function disorder. Thus, the treatment may be of a subject who previously received lacosamide (or functionally equivalent analogue thereof) therapy (without oxcarbazepine), for example lacosamide monotherapy, for example to treat an executive function disorder.

For example, the treatment may be the treatment of autism, wherein the subject may previously have received lacosamide (or functionally equivalent analogue thereof) therapy (without oxcarbazepine), for example lacosamide monotherapy, to treat autism or another executive function disorder. By way of another example, the treatment may be the treatment of ADHD, wherein the subject may previously have received lacosamide (or functionally equivalent analogue thereof) therapy (without oxcarbazepine), for example lacosamide monotherapy, to treat ADHD or another executive function disorder.

The "previous" lacosamide therapy (without oxcarbazepine), for example lacosamide monotherapy, may for example, have commenced at least or about 1, 2, 3, 4, 5, 6, 7, 8, 9, 10, 11 or 12 years, months, weeks or days before commencement of the treatment with lacosamide (or functionally equivalent analogue thereof) and oxcarbazepine; and/or it may have been terminated at least or about 1, 2, 3, 4, 5, 6, 7, 8, 9, 10, 11 or 12 years, months, weeks or days before commencement of the treatment with lacosamide (or functionally equivalent analogue thereof) and oxcarbazepine, preferably at least or about 30, 45 or 60 days.

Thus, also provided is a method of treating an executive function disorder, comprising (i) a treatment schedule comprising administration of lacosamide in the absence of the administration of oxcarbazepine, e.g. lacosamide monotherapy; followed by (ii) a treatment schedule comprising administration of lacosamide and oxcarbazepine, which may be simultaneous, sequential or separate.

Each of treatment schedules (i) and (ii) may be for several days, weeks or months. There may be a gap of several days, weeks or months between scheduled (i) and (ii).

In some embodiments, according to all aspects of the invention, the subject may previously have received oxcarbazepine (or functionally equivalent analogue thereof) therapy (without lacosamide), for example oxcarbazepine monotherapy, for example to treat an executive function disorder, which may be the same or a different an executive function disorder. Thus, the treatment may be of a subject who previously received oxcarbazepine (or functionally equivalent analogue thereof) therapy (without lacosamide), for example oxcarbazepine monotherapy, for example to treat an executive function disorder.

For example, the treatment may be the treatment of autism, wherein the subject may previously have received oxcarbazepine (or functionally equivalent analogue thereof) therapy (without lacosamide), for example oxcarbazepine monotherapy, to treat autism or another executive function disorder. By way of another example, the treatment may be the treatment of ADHD, wherein the subject may previously have received oxcarbazepine (or functionally equivalent analogue thereof) therapy (without lacosamide), for example oxcarbazepine monotherapy, to treat ADHD or another executive function disorder.

The "previous" oxcarbazepine therapy (without lacosamide), for example oxcarbazepine monotherapy, may for example, have commenced at least or about 1, 2, 3, 4, 5, 6, 7, 8, 9, 10, 11 or 12 years, months, weeks or days before commencement of the treatment with oxcarbazepine (or functionally equivalent analogue thereof) and lacosamide; and/or it may have been terminated at least or about 1, 2, 3, 4, 5, 6, 7, 8, 9, 10, 11 or 12 years, months, weeks or days before commencement of the treatment with oxcarbazepine (or functionally equivalent analogue thereof) and lacosamide, preferably at least or about 6 months, 1 year or 1.5 year.

Thus, also provided is a method of treating an executive function disorder, comprising (i) a treatment schedule comprising administration of oxcarbazepine in the absence of the administration of lacosamide, e.g. oxcarbazepine monotherapy; followed by (ii) a treatment schedule comprising administration of lacosamide and oxcarbazepine, which may be simultaneous, sequential or separate.

Each of treatment schedules (i) and (ii) may be for several days, weeks or months. There may be a gap of several days, weeks or months between scheduled (i) and (ii).

In some embodiments, according to all aspects of the invention, the use of the combination of lacosamide (or functionally equivalent analogue thereof) and oxcarbazepine (or functionally equivalent analogue thereof) in treating an executive function disorder is more effective than the use of lacosamide therapy without oxcarbazepine, e.g. lacosamide monotherapy. Preferably, the use of combination therapy over lacosamide therapy without oxcarbazepine provides one or more or all of the following improved outcomes:

(i) an improvement of cognitive function;
(ii) an improvement of cognitive performance;
(iii) a reduction in hyperactivity and/or impulsivity;
(iv) a reduction in involuntary enuresis;
(v) an improvement in the sleep quality;
(vi) improved social skill and communication;
(vii) an improvement in mood;
(viii) decreased anhedonia;
(ix) decreased tachypsichia;
(x) regulation of dysphoria; and/or
(xi) a reduction in stereotypies.

In some embodiments, the amount of lacosamide administered to a subject undergoing a combination therapy is lower than the amount of lacosamide administered during monotherapy to trigger at least the same effect or outcome. It will be understood that when treatment is first administered, the amounts may have to be increased gradually until a maintenance dose is reached; and for the purpose of this comparison, the maintenance amounts of lacosamide are indicated. Preferably, the amount of lacosamide administered to a patient undergoing the combination therapy is at least 20, 30 or 40% lower than the amount of lacosamide used in monotherapy. More preferably still, the amount of lacosamide administered to a patient undergoing the combination therapy is at least 65% lower than the amount of lacosamide used in monotherapy. For example, a patient undergoing a lacosamide monotherapy may require administration of 600 mg lacosamide per day, whereas, the same patient undergoing combination therapy with oxcarbazepine may be administered 200 mg lacosamide per day to trigger at least the same effect or outcome. Preferably, the therapy is for treating a subject suffering from the executive function disorder, such as autism or ADHD. Preferably, the effect or outcome triggered by the combination therapy is substantially better than the effect or outcome triggered by monotherapy. Thus, in some embodiments, the amount of lacosamide administered to a subject undergoing a combination therapy is about 300 mg per day or lower. Preferably, the amount of lacosamide is about 200 mg per day.

According to all aspects of the invention, the subject is a mammal, preferably a human. In particular embodiments, the subject is a child (i.e. one who is growing/maturing physiologically and neurologically towards an adult phenotype). For instance, a "child" may be considered to be a pre-pubescent subject or one who is in the process of completing puberty. Particularly when the subject is a human, a "child" may also be considered to be an individual under the age of 18 in some cases. In preferred embodiments, the child is between 2-12 or at least 2, 3, 4, 5, 6, 7 or 8 and no more than 18, 17 or 16 years old. In more preferred embodiments, the child is between 10 and 16 years old. Thus, the subject may, for example, weigh less than or about 60, 50, 40 or 30 kg. More preferably still the child suffers from ADHD symptoms. The invention is, however, also applied to adults in some embodiments, in which case the subject may, for example, weigh more than or about 50, 60, 70, 80, 90, 100, or 110 kg. Preferably, the adult suffers from autism or ADHD.

The treatment (administration of the combination of lacosamide or a functionally equivalent analogue thereof and oxcarbazepine or functionally equivalent analogue thereof, on a regular basis, such as daily) may be carried out for a suitable period of time, such as at least 2, 3, 4, 5, 6, 7, 8, 9 or 10 weeks, months or years. If it is well tolerated, the treatment may be carried out indefinitely. Preferably, treatment is carried out for a minimum of about 3 months, or about 9 weeks.

In particular embodiments, each of lacosamide (or a functionally equivalent analogue thereof) and oxcarbazepine (or functionally equivalent analogue thereof) may be administered as a single dose once per day (which may be a combined single dose or separate single doses). In preferred embodiments, each may be administered as two, three or more separate doses throughout the day, preferably two. That is to say, the amount of each of lacosamide (or a functionally equivalent analogue thereof) and oxcarbazepine (or functionally equivalent analogue thereof) per day may be divided into two, three or more doses administered to the subject separately throughout the day. For example, for lacosamide the amount of 200 mg/day may be administered as two 100 mg doses per day. Similarly, for oxcarbazepine the amount of 600 mg/day may be administered as two 300 mg doses per day. The multiple doses per day do not necessarily need to be the same amount. In view of the teaching provided herein, the skilled person (e.g. a medical practitioner) is well able to determine an appropriate dosage regimen for the subject according to the subject's specific circumstances.

In some embodiments, lacosamide (or a functionally equivalent analogue thereof) and oxcarbazepine (or functionally equivalent analogue thereof) are administered simultaneously. In other embodiments, lacosamide (or a functionally equivalent analogue thereof) and oxcarbazepine (or functionally equivalent analogue thereof) are administered separately, for example sequentially. Preferably, the administration is simultaneous.

In some embodiments, lacosamide (or a functionally equivalent analogue thereof) and oxcarbazepine (or functionally equivalent analogue thereof) may be co-formulated as a single pharmaceutical composition. Alternatively, lacosamide (or a functionally equivalent analogue thereof) and oxcarbazepine (or functionally equivalent analogue thereof) may be formulated as separate pharmaceutical compositions. In both cases, pharmaceutical compositions may further comprise one or more pharmaceutically acceptable additives/solvents. For instance, lacosamide (or a functionally equivalent analogue thereof) and oxcarbazepine (or functionally equivalent analogue thereof) may be formulated as individual pills, tablets or capsules, each combined with one or more pharmaceutically acceptable solid carriers; or as a solution in one or more pharmaceutically acceptable solvents; or as an emulsion, suspension or dispersion in one or more pharmaceutically acceptable solvents or carriers. In some embodiments, each formulation may also include other pharmaceutically acceptable excipients such as stabilizers, anti-oxidants, binders, colouring agents or emulsifying or taste-modifying agents and extended release formulations. In some embodiments, lacosamide (or a functionally equivalent analogue thereof) and oxcarbazepine (or functionally equivalent analogue thereof) may be formulated (together or separately) as a pharmaceutically acceptable salt, ester, prodrug or metabolite, such as a pharmaceutically acceptable salt, ester, prodrug or metabolite of lacosamide and/or oxcarbazepine.

Thus, in a further aspect, the invention provides a pharmaceutical composition comprising (a) lacosamide or a functionally equivalent analogue thereof and (b) oxcarbazepine or functionally equivalent analogue thereof. Preferably, the pharmaceutical composition comprises (a) lacosamide and (b) oxcarbazepine. Alternatively, lacosamide (or a functionally equivalent analogue thereof) and oxcarbazepine (or functionally equivalent analogue thereof) are formulated as separate pharmaceutical compositions, optionally as part of a kit.

For instance, lacosamide (or a functionally equivalent analogue thereof) and oxcarbazepine (or functionally equivalent analogue thereof) may be formulated as a single capsule or multiple capsules (i.e., a solid oral dosage form consisting of a shell and a filling), whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with a solid or liquid ingredients that can be poured or squeezed. Lacosamide (or a functionally equivalent analogue thereof) and oxcarbazepine (or functionally equivalent analogue thereof) may be formulated as a capsule, or capsules or coated pellets, in which the agents are enclosed within either a hard or soft soluble container or "shell" made from a suitable form of gelatin. The agents themselves may be in the form of granules to which varying amount of coating have been applied or in a capsule coated extended release, in which the agents are enclosed within either a hard or soft soluble container or "shell" made from a suitable form of gelatin. Additionally, the capsule or capsules may be covered in a designated coating which releases the agents in such a manner to allow at least a reduction in dosing frequency of at least one agent, preferably both agents, as compared to that drug or drugs presented as a conventional dosage form.

In a further embodiment, lacosamide (or a functionally equivalent analogue thereof) and oxcarbazepine (or functionally equivalent analogue thereof) may be formulated as a capsule or capsules delayed release, in which the agents are enclosed within either a hard or soft soluble container made from a suitable form of gelatin, and which releases the agents at a time other than promptly after administration, whereby enteric-coated articles are delayed release dosage forms. Capsule delayed release pellets, in which the agents are enclosed within either a hard or soft container or "shell" are also useful. In these cases, the agents themselves are in the form of granules to which enteric coating has been applied, thus delaying release of at least one agent, preferably both agents, until its passing into the intestine. Capsule extended release and capsule film-coated extended release are also useful.

Additionally, the capsule or capsules may be covered in a designated film coating which releases the agents in such a manner to allow at least a reduction in dosing frequency of at least one agent, preferably both agents, as compared to that agent presented as a conventional dosage form. Examples include capsule or capsules gelatin coated (a solid dosage form in which the agents are enclosed within either a hard or soft soluble container made from a suitable form of gelatin; through a banding process, the capsule is coated with additional layers of gelatin so as to form a complete seal) and capsule or capsules liquid filled (a solid dosage form in which the agents are enclosed within a soluble, gelatin shell which is plasticized by the addition of a polyol, such as sorbitol or glycerin, and is therefore of a somewhat thicker consistency than that of a hard shell capsule).

In some embodiments, lacosamide (or a functionally equivalent analogue thereof) and oxcarbazepine (or functionally equivalent analogue thereof) may be dissolved or suspended in a liquid vehicle or vehicles, or formulated as a granule or granules (a small particle or grain), a pellet or pallets (a small sterile solid mass consisting of a highly purified agent, with or without excipients, made by the formation of granules, or by compression and moulding), or a pellet or pallets coated extended release (a solid dosage form in which the agents themselves are in the form of granules to which varying amounts of coating have been applied, and which releases the agents in such a manner to allow a reduction in dosing frequency of at least one agent, preferably both agents, as compared to that agents presented as a conventional dosage form).

Lacosamide (or a functionally equivalent analogue thereof) and oxcarbazepine (or functionally equivalent analogue thereof) may be formulated as pills (a small, round solid dosage form containing the agents intended for oral administration), powder (an intimate mixture of dry, finely divided agent with one or more pharmaceutically acceptable additives that may be intended for internal or external use), elixir (a clear, pleasantly flavored, sweetened hydroalcoholic liquid containing dissolved agents; it is intended for oral use), chewing gum (a sweetened and flavored insoluble plastic material of various shapes which when chewed, releases the agents substance into the oral cavity), syrup (an oral solution containing the agent and high concentrations of sucrose or other sugars; the term has also been used to include any other liquid dosage form prepared in a sweet and viscid vehicle, including oral suspensions), tablet or tablets (a solid dosage form containing the agents with or without suitable diluents), tablet chewable (a solid dosage form containing the agents with or without suitable diluents that is intended to be chewed, producing a pleasant tasting residue in the oral cavity that is easily swallowed and does not leave a bitter or unpleasant after-taste), tablet or tablets coated or tablet or tablets delayed release, tablet or tablets dispersible, tablet or tablets effervescent, tablet or tablets extended release, tablet or tablets film coated, or tablet or tablets film coated extended release where the tablet or tablets is/are formulated in such manner as to make at least one of the contained agents, preferably both contained agents, available over an extended period of time following ingestion.

In other forms, a tablet or tablets for solution, tablet or tablets for suspension, tablet or tablets multilayer, tablet or tablets multilayer extended release may be provided, where the tablet or tablets is/are formulated in such manner as to allow at least a reduction in dosing frequency of at least one agent, preferably both agents, as compared to that agents presented as a conventional dosage form. A tablet or tablets orally disintegrating, tablet or tablets orally disintegrating delayed release, tablet or tablets soluble, tablet or tablets sugar coated, osmotic, and the like are also suitable.

The oral dosage form composition may contain, in addition to lacosamide (or a functionally equivalent analogue thereof) and/or oxcarbazepine (or functionally equivalent analogue thereof), one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer.

In particular embodiment of the present invention, particularly if the executive function disorder is ADHD, (a) lacosamide and (b) oxcarbazepine may be administered per the following treatment regimen:

(a) lacosamide is administered per the following treatment regimen:
  (i) an initial amount of 50-100 mg/day, (which if tolerated by the patient is) followed by:
  (ii) every 1-2 weeks increasing the amount by 50-100 mg up to a maximum amount in the range 200-500 mg/day and maintaining the daily amount thereat; and/or
(b) oxcarbazepine is administered per the following treatment regimen:
  (i) an initial amount of 600-750 mg/day, (which if tolerated by the patient is) followed by:
  (ii) after 6-7 weeks increasing the amount to the amount in the range 750-1800 mg/day and maintaining the daily amount thereat.

More preferably still, (a) lacosamide and (b) oxcarbazepine are administered per the following treatment regimen:

(a) lacosamide is administered per the following treatment regimen:
  (i) an initial amount of 50-100 mg/day, (which if tolerated by the patient is) followed by:
  (ii) every week increasing the amount by 50-100 mg up to a maximum amount in the range 200-400 mg/day and maintaining the daily amount thereat; and/or
(b) oxcarbazepine is administered per the following treatment regimen:
  (i) an initial amount of 600 mg/day, (which if tolerated by the patient is) optionally followed by:
  (ii) after 6-7 weeks increasing the amount to the amount in the range 900-1200 mg/day and maintaining the daily amount thereat.

In further embodiments, particularly if the executive function disorder is ADHD, (a) lacosamide and (b) oxcarbazepine may be administered per the following treatment regimen:

(a) lacosamide is administered per the following treatment regimen:
  (i) an initial amount of 50-100 mg/day, (which if tolerated by the patient is) followed by:
  (ii) every 1-2 weeks increasing the amount by 50-100 mg up to a maximum amount in the range 200-500 mg/day and maintaining the daily amount thereat; and/or
(b) oxcarbazepine is administered per the following treatment regimen:
  (i) an initial amount of 500-900 mg/day, (which if tolerated by the patient is) followed by:
  (ii) after 6-7 weeks increasing the amount to the amount in the range 600-1800 mg/day and maintaining the daily amount thereat.

In further embodiments, lacosamide is administered per the following treatment regimen:

(i) 100 mg/day for 1-2 weeks, followed by:
(ii) 200 mg/day and maintaining the daily amount thereat, optionally, after 1-2 weeks, followed by:
(iii) 300 mg/day for 1-2 weeks, optionally followed by:
(iv) 400 mg/day and maintaining the daily amount thereat.

In further embodiments, oxcarbazepine is administered per the following treatment regimen:

(i) 600 mg/day for 6-7 weeks, followed by:
(ii) 900 mg/day and maintaining the daily amount thereat, optionally, after 1-4 weeks, followed by:
  i. 1200 mg/day and maintaining the daily amount thereat; or
  ii. 600 mg/day and maintaining the daily amount thereat.

In another embodiment of the present invention, particularly if the executive function disorder is autism, (a) lacosamide and (b) oxcarbazepine may be administered per the following treatment regimen:

(a) lacosamide is administered per the following treatment regimen:
  (i) an initial amount of 50-100 mg/day, (which if tolerated by the patient is) followed by:
  (ii) every 1-2 weeks increasing the amount by 50-100 mg up to a maximum amount in the range 200-500 mg/day and maintaining the daily amount thereat; and/or
(b) oxcarbazepine is administered per the following treatment regimen:
  (i) an initial amount of 600-750 mg/day, (which if tolerated by the patient is) optionally followed by:
  (ii) every week increasing the amount by 150-300 mg to the amount in the range 900-2400 mg/day and maintaining the daily amount thereat.

More preferably still, (a) lacosamide and (b) oxcarbazepine are administered per the following treatment regimen:

(a) lacosamide is administered per the following treatment regimen:
  (i) an initial amount of 50-100 mg/day, (which if tolerated by the patient is) followed by:
  (ii) every week increasing the amount by 50-100 mg up to a maximum in the range 200-400 mg/day and maintaining the daily amount thereat; and/or
(b) oxcarbazepine is administered per the following treatment regimen:
  (i) an initial amount of 600 mg/day, (which if tolerated by the patient is) optionally followed by:
  (ii) every week increasing the amount by 300 mg up to a maximum amount of 1200 mg/day and maintaining the daily amount thereat.

In further embodiments, particularly if the executive function disorder is autism, (a) lacosamide and (b) oxcarbazepine may be administered per the following treatment regimen:

(a) lacosamide is administered per the following treatment regimen:
  (i) an initial amount of 50-100 mg/day, (which if tolerated by the patient is) followed by:
  (ii) every 1-2 weeks increasing the amount by 50-100 mg up to a maximum amount in the range 200-500 mg/day and maintaining the daily amount thereat; and/or
(b) oxcarbazepine is administered per the following treatment regimen:
  (i) an initial amount of 400-900 mg/day, (which if tolerated by the patient is) optionally followed by:
  (ii) every week increasing the amount by 150-600 mg to the amount in the range 600-2400 mg/day and maintaining the daily amount thereat.

In further embodiments, lacosamide is administered per the following treatment regimen:

(i) 100 mg/day for 1-2 weeks, followed by:
(ii) 200 mg/day and maintaining the daily amount thereat, optionally, after 1-2 weeks, followed by:
(iii) 300 mg/day for 1-2 weeks, optionally followed by:
(iv) 400 mg/day and maintaining the daily amount thereat.

In further embodiments, oxcarbazepine is administered per the following treatment regimen:

(i) 600 mg/day for 1-2 weeks, followed by:
(ii) 900 mg/day for 1-2 weeks, followed by:

(iii) 1200 mg/day and maintaining the daily amount thereat, optionally, after 1-2 weeks, followed by:
(iv) 1800 mg/day and maintaining the daily amount thereat, optionally, after 1-2 weeks, followed by:
(v) 2400 mg/day and maintaining the daily amount thereat.

The exact maintenance amount, according to all aspects of the invention, can, in view of the teaching provided herein, be routinely determined by the skilled person based on the specific subject's physical condition, severity of executive function disorder symptoms and tolerance of the agents being administered. Generally speaking, the exact maintenance amount will be a compromise between improvement of the executive function disorder symptoms against the physiological tolerance of the specific subject for that exact amount (e.g. the observance/potential for unwanted side effects). This is specific to each individual subject and it is routine for the skilled person in the art (e.g. a medical practitioner) to determine the exact maintenance amount for a specific subject based on the aforementioned factors in view of the teaching provided herein.

In some embodiments, according to all aspects of the invention, the administered amount of lacosamide is 400 mg/day or less, such as 350, 300, 250, 200, 150, 100, or 150 mg/day or less, preferably the administered amount of lacosamide is 200 mg/day.

It will be understood that any reference herein to the administration of an active in an amount of "X or less" requires the administration of a minimal amount, for example of at least 10, 20, 30, 40 or 50 mg/day.

In some embodiments, according to all aspects of the invention, in a subject weighing less than 50 kg, the administered amount of oxcarbazepine is 1200 mg/day or less, such as 1200, 900, 600 mg/day or less, preferably the administered amount of oxcarbazepine is between 600-1200 mg/day.

In some embodiments, according to all aspects of the invention, in a subject weighing 50 kg or more, the administered amount of oxcarbazepine is 2400 mg/day or less, such as 2400, 2100, 1800, 1500, 1200, 900, 600 mg/day or less, preferably the administered amount of oxcarbazepine is 1200 mg/day.

In a further aspect, the invention provides a kit, kit-of-parts, or system comprising (a) lacosamide or a functionally equivalent analogue thereof and (b) oxcarbazepine or functionally equivalent analogue thereof. Preferably, the kit, kit-of-parts, or system comprises (a) lacosamide and (b) oxcarbazepine.

According to all aspects of the invention, lacosamide (or a functionally equivalent analogue thereof) and oxcarbazepine (or functionally equivalent analogue thereof) may be administered orally, topically, parenterally or transdermally or by inhalation. Lacosamide (or a functionally equivalent analogue thereof) and oxcarbazepine (or functionally equivalent analogue thereof) may be administered by injection or intravenous infusion using suitable sterile solutions. Topical dosage forms may be creams, ointments, patches, or similar vehicles suitable for transdermal and topical dosage forms. Oral administration is preferred. For instance, in the case of lacosamide, in some embodiments it is administered as a film-coated tablet or an oral solution (e.g. under the brand name VIMPAT®) but intravenous administration is also possible. In the case of oxcarbazepine, in some embodiments it is administered as film-coated tablet or an oral suspension (e.g. under the brand name TRILEPTAL®).

According to all aspects of the invention, lacosamide (or a functionally equivalent analogue thereof) and oxcarbazepine (or functionally equivalent analogue thereof) may preferably be the only therapeutically active agents present in the pharmaceutical composition, kit or kit-of-parts; or administered as part of the treatment of the invention, although it will be understood that the pharmaceutical composition, kit or kit-of-parts may include excipients.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention is further disclosed in the following clauses:

1. A combination or kit-of-parts of (a) lacosamide or a functionally equivalent analogue thereof and (b) oxcarbazepine or functionally equivalent analogue thereof for simultaneous, separate or sequential use in treating an executive function disorder.
2. The combination or kit-of-parts for use of clause 1, wherein the executive function disorder is attention deficit hyperactivity disorder (ADHD), or autism.
3. The combination or kit-of-parts for use of clause 1 or clause 2, wherein the executive function disorder is ADHD.
4. The combination or kit-of-parts for use of any one of clauses 1-3, preferably clause 3, wherein:
   (a) lacosamide or functionally equivalent analogue thereof is administered per the following treatment regimen:
      (i) an initial amount of 50-100 mg/day, (which if tolerated by the patient is) followed by:
      (ii) every 1-2 weeks increasing the amount by 50-100 mg up to a maximum amount in the range 200-500 mg/day and maintaining the daily amount thereat; and/or
   (b) oxcarbazepine or functionally equivalent analogue thereof is administered per the following treatment regimen:
      (i) an initial amount of 600-750 mg/day, (which if tolerated by the patient is) followed by:
      (ii) after 6-7 weeks increasing the amount to the amount in the range 750-1800 mg/day and maintaining the daily amount thereat.
5. The combination or kit-of-parts for use of any one of clauses 1-3, preferably clause 3 or clause 4, wherein:
   (a) lacosamide or functionally equivalent analogue thereof is administered per the following treatment regimen:
      (i) an initial amount of 50-100 mg/day, (which if tolerated by the patient is) followed by:
      (ii) every week increasing the amount by 50-100 mg up to a maximum amount in the range 200-400 mg/day and maintaining the daily amount thereat; and/or
   (b) oxcarbazepine or functionally equivalent analogue thereof is administered per the following treatment regimen:
      (i) an initial amount of 600 mg/day, (which if tolerated by the patient is) followed by:
      (ii) after 6-7 weeks increasing the amount to the amount in the range 900-1200 mg/day and maintaining the daily amount thereat.
6. The combination or kit-of-parts for use of any one of clauses 1-5, wherein lacosamide or functionally equivalent analogue thereof is administered per the following treatment regimen:
   (i) 100 mg/day for 1-2 weeks, followed by:
   (ii) 200 mg/day and maintaining the daily amount thereat, optionally, after 1-2 weeks, followed by:
   (iii) 300 mg/day for 1-2 weeks, optionally followed by:
   (iv) 400 mg/day and maintaining the daily amount thereat.
7. The combination or kit-of-parts for use of any one of clauses 1-6, wherein oxcarbazepine or functionally equivalent analogue thereof is administered per the following treatment regimen:
   (i) 600 mg/day for 6-7 weeks, followed by:
   (ii) 900 mg/day and maintaining the daily amount thereat, optionally, after 1-4 weeks, followed by:
      i. 1200 mg/day and maintaining the daily amount thereat; or
      ii. 600 mg/day and maintaining the daily amount thereat.
8. The combination or kit-of-parts for use of clause 1 or clause 2, wherein the executive function disorder is autism.
9. The combination or kit-of-parts for use of any one of clauses 1-3 or clause 8, preferably clause 8 wherein:
   (a) lacosamide or functionally equivalent analogue thereof is administered per the following treatment regimen:
      (i) an initial amount of 50-100 mg/day, (which if tolerated by the patient is) followed by:
      (ii) every 1-2 weeks increasing the amount by 50-100 mg up to a maximum amount in the range 200-500 mg/day and maintaining the daily amount thereat; and/or
   (b) oxcarbazepine or functionally equivalent analogue thereof is administered per the following treatment regimen:
      (i) an initial amount of 600-750 mg/day, (which if tolerated by the patient is) optionally followed by:
      (ii) every week increasing the amount by 150-300 mg to the amount in the range 900-2400 mg/day and maintaining the daily amount thereat.
10. The combination or kit-of-parts for use of any one of clauses 1-3, clause 8 or clause 9, wherein
   (a) lacosamide or functionally equivalent analogue thereof is administered per the following treatment regimen:
      (i) an initial amount of 50-100 mg/day, (which if tolerated by the patient is) followed by:
      (ii) every week increasing the amount by 50-100 mg up to a maximum amount in the range 200-400 mg/day and maintaining the daily amount thereat; and/or
   (b) oxcarbazepine or functionally equivalent analogue thereof is administered per the following treatment regimen:
      (i) an initial amount of 600 mg/day, (which if tolerated by the patient is) optionally followed by:
      (ii) every week increasing the amount by 300 mg up to a maximum amount of 1200 mg/day and maintaining the daily amount thereat.
11. The combination or kit-of-parts for use of any one of clauses 1-3 or 8-10, wherein lacosamide or functionally equivalent analogue thereof is administered per the following treatment regimen:
   (i) 100 mg/day for 1-2 weeks, followed by:
   (ii) 200 mg/day and maintaining the daily amount thereat, optionally, after 1-2 weeks, followed by:

(iii) 300 mg/day for 1-2 weeks, optionally followed by:
(iv) 400 mg/day and maintaining the daily amount thereat.

12. The combination or kit-of-parts for use of any one of clauses 1-3 or 8-11, wherein oxcarbazepine or functionally equivalent analogue thereof is administered per the following treatment regimen:
(i) 600 mg/day for 1-2 weeks, followed by:
(ii) 900 mg/day for 1-2 weeks, followed by:
(iii) 1200 mg/day and maintaining the daily amount thereat, optionally, after 1-2 weeks, followed by:
(iv) 1800 mg/day and maintaining the daily amount thereat, optionally, after 1-2 weeks, followed by:
(v) 2400 mg/day and maintaining the daily amount thereat.

13. The combination or kit-of-parts for use of anyone of clauses 1-12, for simultaneous, separate or sequential use in treating an executive function disorder in a subject, wherein the subject does not suffer from epilepsy, bipolar disorder, seizures, neuropathic pain, depression, anxiety, schizophrenia, obsessive-compulsive disorder (OCD), Alzheimer's disease, frontotemporal dementia, Lewy body dementia, Tourette's syndrome and/or traumatic injuries to the brain.

14. The combination or kit-of-parts for use of any one of clauses 1-13, wherein the executive function disorder is characterised by or associated with one or more, preferably at least 2, 3, 4, 5 or all of the symptoms selected from
(i) hyperactivity and/or impulsivity;
(ii) involuntary enuresis;
(iii) aggressive behaviour;
(iv) insomnia or hypersomnia;
(v) impaired attention processing;
(vi) impaired communication;
(vii) impaired social skills;
(viii) impaired visual and/or auditory processing;
(ix) anhedonia;
(x) tachypsichia;
(xi) dysphoria; and/or
(xii) stereotypies.

15. The combination or kit-of-parts for use of any one of clauses 1-14, wherein the treatment alleviates one or more, preferably at least 2, 3, 4, 5 or all of the symptoms (of the executive function disorder) selected from hyperactivity and/or impulsivity;
(ii) involuntary enuresis;
(iii) aggressive behaviour;
(iv) insomnia or hypersomnia;
(v) impaired attention processing;
(vi) impaired communication;
(vii) impaired social skills;
(viii) impaired visual and/or auditory processing;
(ix) anhedonia;
(x) tachypsichia;
(xi) dysphoria; and/or
(xii) stereotypies.

16. The combination or kit-of-parts for use of any one of clauses 1-15, for simultaneous, separate or sequential use in treating an executive function disorder in a subject that has previously been treated with lacosamide, e.g. lacosamide monotherapy, wherein said previous treatment was preferably to treat a or the executive function disorder.

17. The combination or kit-of-parts for use of any one of clauses 1-16, wherein the administered amount of lacosamide or functionally equivalent analogue thereof is 400 mg/day or less, such as 400, 350, 300, 250, 200, 150, 100, or 150 mg/day or less, preferably the administered amount of lacosamide or functionally equivalent analogue thereof is 200 mg/day.

18. The combination or kit-of-parts for use of any one of clauses 1-17, wherein the administered amount of oxcarbazepine or functionally equivalent analogue thereof in adults is 2400 mg/day or less, such as 2400, 2100, 1800, 1500, 1200, 900, 750, or 600 mg/day or less, preferably the administered amount of oxcarbazepine or functionally equivalent analogue thereof is between 600-1800 mg/day, more preferably, the administered amount of oxcarbazepine or functionally equivalent analogue thereof is 1200 mg/day.

19. The combination or kit-of-parts for use of any one of clauses 1-18, wherein the administered amount of oxcarbazepine or functionally equivalent analogue thereof is 1350 mg/day or less, such as 1350, 1200, 1050, 900, 750, 600 mg/day or less, preferably the administered amount of oxcarbazepine or functionally equivalent analogue thereof is between 600-1200 mg/day.

20. The combination or kit-of-parts for use of any one of clauses 1-19, wherein lacosamide or functionally equivalent analogue thereof and oxcarbazepine or functionally equivalent analogue thereof are administered in 1-3 doses per day, preferably 2 doses per day.

21. The combination or kit-of-parts for use of any one of clauses 1-20, wherein lacosamide or functionally equivalent analogue thereof and oxcarbazepine or functionally equivalent analogue thereof are administered simultaneously.

22. The combination or kit-of-parts for use of any one of clauses 1-20, wherein lacosamide or functionally equivalent analogue thereof and oxcarbazepine or functionally equivalent analogue thereof are administered separately, for example sequentially 23. The combination or kit-of-parts for use of any one of clauses 1-22, wherein the functionally equivalent analogue of lacosamide is selected from lacosamide S enantiomer, lacosamide racemate, or rufinamide; and/or wherein the functionally equivalent analogue of oxcarbazepine is selected from (L- and/or R-) licarbazepine, eslicarbazepine or eslicarbazepine acetate.

24. The combination or kit-of-parts for use of any one of clauses 1-23, wherein the treatment results in one or more or all of the following:
(i) an improvement of cognitive function;
(ii) an improvement of cognitive performance;
(iii) a reduction in hyperactivity;
(iv) a reduction in involuntary enuresis;
(v) an improvement in the sleep quality; and/or
(vi) an improvement in mood;
(vii) decreased anhedonia;
(viii) decreased tachypsichia;
(ix) regulation of dysphoria; and/or
(x) a reduction in stereotypies.

25. The combination for use of any one of clauses 1-21, or clauses 23 or 24, wherein lacosamide or functionally equivalent analogue thereof and oxcarbazepine or functionally equivalent analogue thereof are co-formulated in a single pharmaceutical composition.

26. The combination or kit-of-parts for use of any one of clauses 1-24, wherein lacosamide or functionally equivalent analogue thereof and oxcarbazepine or functionally equivalent analogue thereof are in separate pharmaceutical compositions.

27. A kit, kit-of-parts, or system comprising (a) lacosamide or a functionally equivalent analogue thereof and (b) oxcarbazepine or functionally equivalent analogue thereof, for example comprising a first pharmaceutical composition comprising lacosamide or a functionally equivalent analogue thereof; and a second pharmaceutical composition comprising oxcarbazepine or functionally equivalent analogue thereof.
28. A method for treating an executive function disorder comprising administering (a) lacosamide or a functionally equivalent analogue thereof and (b) oxcarbazepine or functionally equivalent analogue thereof to a subject suffering from an executive function disorder or symptoms thereof.
29. The method of clause 28, wherein (a) lacosamide or a functionally equivalent analogue thereof and (b) oxcarbazepine or functionally equivalent analogue thereof are administered simultaneously, separately or sequentially.
30. A combination or kit-of-parts of (a) lacosamide or a functionally equivalent analogue thereof and (b) oxcarbazepine or functionally equivalent analogue thereof for simultaneous, separate or sequential use in alleviating one or more symptoms of an executive function disorder.
31. The combination or kit-of-parts for use of clause 30, wherein the executive function disorder is attention deficit hyperactivity disorder (ADHD), attention deficit disorder (ADD), or autism.
32. The combination for use of clause 30 or clause 31, wherein the one or more symptoms are selected from:
    (i) hyperactivity and/or impulsivity;
    (ii) involuntary enuresis;
    (iii) aggressive behaviour;
    (iv) insomnia or hypersomnia;
    (v) impaired attention processing;
    (vi) impaired communication;
    (vii) impaired social skills;
    (viii) impaired visual and/or auditory processing
    (ix) anhedonia;
    (x) tachypsichia;
    (xi) dysphoria; and/or
    (xii) stereotypies.
33. A pharmaceutical composition comprising (a) lacosamide or a functionally equivalent analogue thereof and (b) oxcarbazepine or functionally equivalent analogue thereof.
34. Lacosamide or a functionally equivalent analogue thereof for use in a method of treating an executive function disorder, wherein the method comprises administering therapeutically effective amounts of (a) lacosamide or a functionally equivalent analogue thereof and (b) oxcarbazepine or functionally equivalent analogue thereof to a subject suffering from the executive function disorder, preferably wherein the administration is sequential, simultaneous or separate.
35. Oxcarbazepine or functionally equivalent analogue thereof for use in a method of treating an executive function disorder, wherein the method comprises administering therapeutically effective amounts of (a) oxcarbazepine or functionally equivalent analogue thereof and (b) lacosamide or a functionally equivalent analogue thereof to a subject suffering from the executive function disorder, preferably wherein the administration is sequential, simultaneous or separate.

EXAMPLES

The invention will be further understood with reference to the following experimental examples.

Example 1—Comparative Study of Lacosamide Monotherapy and Lacosamide and Oxcarbazepine Combination Therapy in Treating ADHD The effects of lacosamide monotherapy were tested in three patients (two boys, 10 and 16 years old; and one girl, 13 years old) suffering from ADHD over the period of 6 months. After the period of 6 months, the treatment was discontinued for 45 days. Next, the three patients were treated with a combination of lacosamide and oxcarbazepine for a period of 3 months. The results of monotherapy and combination therapy were compared.

Materials and Methods

Patients were monitored clinically every week, during the whole duration of the study. They were also monitored on their pedagogic condition and evolution: before any treatment, mid-term and by the end of the lacosamide monotherapy and combination treatment. In addition, the patients were monitored neuropsychologicaly through the administration of different tests, pre- and post-treatment. A basal measure of their executive capabilities was established before any treatment.

Treatment Administration

Lacosamide was administered to the patients following the approved treatment regimen for lacosamide (Vimpat®) in epileptic children from 4 years of age. This is shown in the table below.

TABLE 1

| Treatment regimen for lacosamide | |
|---|---|
| Starting dose | 2 mg/kg/day |
| Titration (incremental steps) | 2 mg/kg/day every week |
| Maximum recommended dose in patients <40 kg | Up to 12 mg/kg/day |
| Maximum recommended dose in patients ≥40 kg to <50 kg | Up to 10 mg/kg/day |

Oxcarbazepine was administered to the patients following the approved treatment regimen for oxcarbazepine (TRILEPTAL®) in children with seizures from 2 to 16 years of age.

The treatment was delivered twice a day and went on for at least 3 months.

Monotherapy

Initially, a dose of 50 mg/12 hrs of lacosamide was administered to every patient. Through the study, the dose of lacosamide was increased (by 100 mg per week) to 300 mg/12 hrs for every patient, following clinical response (on attention capacity, sleep, tiredness, mood stability, comprehension and general cognitive improvement).

Combination Treatment

Initially, a dose of 50 mg/12 hrs of lacosamide and a dose of 300 mg/12 hrs of oxcarbazepine was administered to every patient. Through the study, the dose of lacosamide was increased (by 100 mg per week) to 200 mg/12 hrs for every patient, following clinical response (attention capacity, sleep, tiredness, mood stability, comprehension and general cognitive improvement). In response to clinical presentation of all three patients, the dose of lacosamide was decreased to 100 mg/12 hrs and maintained thereafter. The dose for oxcarbazepine was increased in week 7 to 450 mg/12 hrs for every patient, maintaining the previously reached respective doses for lacosamide.

Results

Starting from this initial dose (50 mg/12 hs), the dose of lacosamide was adjusted to reflect clinically effective dose, based on clinical signs. Lacosamide was initially raised by 100 mg/24 hs in two takes. The highest dose of lacosamide was 400 mg/24 hs. In the combination therapy, oxcarbazepine was raised from 600 mg to 900 mg for all participants after 6 weeks, regardless of their lacosamide dosage.

The final dosage of lacosamide and oxcarbazepine was established based on patients' clinical results for executive dysfunction and the neurophysiological symptoms (e.g. hyperactivity, enuresis, and lethargy). The clinically effective dose of lacosamide in combination therapy in all patients was 200 mg per day. Similarly, the final dosage of oxcarbazepine was between 600 and 1200 mg per day (Patient 1: 600 mg per day, Patient 2: 900 mg per day and Patient 3: 1200 mg per day). The clinically effective dose of lacosamide in monotherapy was 600 mg per day for 2 patients and 350 mg for one patient (Table 2).

TABLE 2

Comparison of lacosamide doses in monotherapy and combination therapy.

| Patient | Clinically effective dose of lacosamide in monotherapy | Clinically effective dose of lacosamide in combination therapy with oxcarbazepine |
|---|---|---|
| Patient 1 | 600 mg/day | 200 mg/day |
| Patient 2 | 600 mg/day | 200 mg/day |
| Patient 3 | 350 mg/day | 200 mg/day |

The determination of clinically effective doses during the combination therapy was very important: both molecules were tolerated well under clinically effective doses, but not under too low or too high doses; showing undesired side effects (enuresis, headaches, tiredness, lack of will, dizziness) that could only be reversed by the re-evaluation of the dosage.

Importantly, the clinically effective dose of lacosamide used as part of the combined therapy was substantially lower than the dose of lacosamide in monotherapy. The dose of lacosamide in monotherapy was at the very top range of the authorized amount that can be administered to a patient.

Clinical Evolution Under Treatment

Stopping Severe Hyperkinesia

Only one of the 3 patients suffered from hyperkinesia.

Lacosamide alone did not improve hyperactivity regulation, at any dosage. Although many functions and mental capacity were improved during lacosamide monotherapy, the patient never improved enough to stop moving continuously, even at the highest dose of lacosamide.

The administration of a combination of oxcarbazepine and lacosamide decreased patient's hyperactivity.

Severe Cognitive Disability/Severe Dysphasia

Of the 3 patients, 2 had very serious cognitive disabilities.

Case 001 administration of lacosamide alone improved many cognitive disabilities, but dysphasia, and extreme impulsiveness remained unchanged after administration of lacosamide monotherapy. Administration of a combination therapy resulted in an additional benefit of a reduction of impulsiveness.

Cases 002 and 003 improved under lacosamide alone, but the degree of the disability never really disappeared. Administration of a combination therapy resulted in a consistent cognitive improvement, which far exceeded the improvement observed during monotherapy. The ability to speak substantially improved in both patients undergoing the combination therapy—something that was unaffected by the monotherapy.

Enuresis

Lacosamide monotherapy partially stopped enuresis episodes in the two patients that suffered from this symptom. The clinically effective dose of lacosamide and oxcarbazepine administered in combination completely stopped enuresis.

Mood Regulation

Aggressive behaviour towards others (fighting), deliberately contained anger and sadness were three forms of mood instability that completely disappeared by the application of the combined therapy of lacosamide and oxcarbazepine. These symptoms were only partially regressed during lacosamide monotherapy.

Sleep

All three cases experienced in the absence of any treatment significantly dysfunctional sleeping pattern. Patient 001 presented an anxious behaviour while falling asleep slowing his sleep induction, and was waking up very early. Patient 002 went through a 12 hours hypersomnia every night. Patient 003 had an interrupted sleeping cycle. The sleeping pattern improved for all three cases on administration of the combination therapy. The improvement in hypersomnia and hyperactivity during sleep was substantially better upon administration of the combination therapy in comparison to lacosamide monotherapy.

Lethargy

Two patients presented absence of energy and tense tiredness that did not necessary induced sleeping. Lethargic situations disappeared with lacosamide monotherapy and combination treatment. However, the quality of the presence, the availability of the attention, and the awareness as well as connection with reality that replaced lethargy was clinically more consistent under the combined therapy.

Social Interaction

The possibility of sharing with others and intervene socially tightly depends on the ability to communicate. In the absence of the ability to communicate, patients tend to isolate. Similarly, when the patients do not feel secure "signs" coming from their peers, they will always presume that nothing good is meant.

Two of the three patients were extremely limited with their social exchanges; the third one, with hyperkinetic and impulsive characteristics, had frequent aggressive interaction and unstable (shortened, abrupt) exchanges.

The combination therapy showed improvement in all cases (independently from patients and tutors). The effect of the combination therapy was significantly better than the effect of monotherapy.

Neuropsychological Evaluation

The results of neuropsychological tests for lacosamide monotherapy and lacosamide and oxcarbazepine combination therapy were evaluated. Two out of three patients showed significantly improved neuropsychological indicators. The other patient had similar results for monotherapy and combination treatment.

The comparative results are presented below.

Case 001

In the first assessment (June 2020) using the Conners' Continuous Performance Test (CPT2-O), the patient showed that the more he advanced, the more his attention capacity declined. On the second evaluation (end-study) of the same test, this patient reduced his indicators of inattention from 6 to 2, going from a score of 76.92% and a "Severe Impairment" to a 50% score, denoted as "Moderate Impairment" (Table 3). This is correlated with the fact that the patient clinically improved his hyperkinesia and therefore his intellectual ability and capacity.

The nominal capacity measured by the Stroop-P improved by almost 10% (51 to 60), making it go from "Slight Impairment" to "Average"—this is illustrated by the improved verbal reasoning (speech).

TABLE 3

| Neuropsychological evaluation results for patient 001 (case 001). | | | | | | | |
|---|---|---|---|---|---|---|---|
| Test | Evaluated Function | Involved Brain Structure | Severity Range October 2020 | October 2020 Level | Severity Range December 2020 | December 2020 Level | Actual Interpretation |
| TONI-2 | Nonverbal Reasoning Ability | Frontal Lobe | 17/55 | CI-111 | 20/55 | CI-106 | Average |
| CPT-2-o | Impulse Control | Frontal Lobe | 76.92% 6 inattention indicators 2 indicators within limitations in surveillance. | Clinical | 50% 2 inattention indicators 2 surveillance limitation indicators. | Clinical | Mild Deterioration |
| CPT-2-c | Visual Attentional Ability | Frontal Lobe | No impulsivity indicators | 1 | No impulsivity indicators | 1 | Average |
| WCST | Reasoning (Abstraction Categorization) | Frontal Lobe | 3 categories completed | 2 | 3 categories completed | 2 | Light Deterioration |
| WCST | Cognitive flexibility | Frontal Lobe | 24 persistent errors | 1 | 22 persistent errors | 1 | Average |
| Stroop-p | Nominative capacity | Left Hem | 51/100 | 2 | 60/100 | 1 | Average |
| Stroop-c | Nominative capacity | Right Hem | 43/100 | 1 | 51/100 | 1 | Average |
| Stroop-c/p | Resistance to Perseveration | Frontal Lobe | 18/100 | 1 | 25/100 | 1 | Average |

Case 002

Case 002 evolved significantly in clinical terms, including a pedagogic evolution never obtained while the patient was on lacosamide monotherapy: the patient progressed to Comprehensive Reading within 3 months on administration of the combined therapy (Table 4).

TABLE 4

| Neuropsychological evaluation results for patient 002 (case 002). | | | | | | | |
|---|---|---|---|---|---|---|---|
| Test | Evaluated Function | Involved Brain Structure | Severity Range October 2020 | October 2020 Level | Severity Range December 2020 | December 2020 Level | Actual Interpretation |
| TONI-2 | Nonverbal Reasoning Ability | Frontal Lobe | 28/55 | CI-104 | 27/55 | CI-102 | Average |
| CPT-2-o | Impulse Control | Frontal Lobe | 37.01% 2 inattention indicators | Non Clinical | 53.86% 2 inattention indicators 1 surveillance limitation indicator | Clinical | Mild Deterioration |
| CPT-2-c | Visual Attentional Ability | Frontal Lobe | 1 impulsivity indicator | 2 | 2 impulsivity indicators | 2 | Light Deterioration |
| WCST | Reasoning (Abstraction Categorization) | Frontal Lobe | 8 categories completed | 0 | 7 categories completed | 0 | High Average |
| WCST | Cognitive flexibility | Frontal Lobe | 5 persistent errors | 0 | 9 persistent errors | 1 | Average |
| Stroop-p | Nominative capacity | Left Hem | 32/100 | 4 | 42/100 | 4 | Severe Deterioration |
| Stroop-c | Nominative capacity | Right Hem | 40/100 | 3 | 51/100 | 3 | Mild Deterioration |
| Stroop-c/p | Resistance to Perseveration | Frontal Lobe | 30/100 | 2 | 32/100 | 2 | Light Deterioration |

Case 003

This patient was particularly inhibited in the social space, and with very significant academic and neurocognitive difficulties. The tests carried out after 6 months of the treatment with lacosamide alone and after 3 months of the combined therapy with lacosamide and oxcarbazepine showed that the patient significantly improved in 5 out of 8 tests after administration of the combined therapy (Table 5).

TABLE 5

Neuropsychological evaluation results for patient 003 (case 003).

| Test | Evaluated Function | Involved Brain Structure | Severity Range October 2020 | October 2020 Level | Severity Range December 2020 | December 2020 Level | RESULTS TABLE Test |
|---|---|---|---|---|---|---|---|
| TONI-2 | Nonverbal Reasoning Ability | Frontal Lobe | 19/55 | CI-95 | 30/55 | CI-118 | High Average |
| CPT-2-o | Impulse Control | Frontal Lobe | 50% (6 inattention indicators) | Clinical | 60.41% (7 inattention indicators) | Clinical | Severe Deterioration |
| CPT-2-c | Visual Attentional Ability | Frontal Lobe | 1 impulsivity indicator | 2 | 1 impulsivity indicator | 2 | Light Deterioration |
| WCST | Reasoning (Abstraction Categorization) | Frontal Lobe | 4 categories completed | 2 | 7 categories completed | 0 | High Average |
| WCST | Cognitive flexibility | Frontal Lobe | 23 persistent errors | 2 | 11 persistent errors | 1 | Average |
| Stroop-p | Nominative capacity | Left Hem | 51/100 | 3 | 52/100 | 2 | Light Deterioration |
| Stroop-c | Nominative capacity | Right Hem | 51/100 | 2 | 43/100 | 3 | Mild Deterioration |
| Stroop-c/p | Resistance to Perseveration | Frontal Lobe | 21/100 | 3 | 27/100 | 2 | Light Deterioration |

The patient's non-verbal reasoning capacity raised from 95 to 118 points (24% increase with respect to the same test after 6 months of Lacosamide monotherapy), showing her gained capacity for Categorization and Abstraction (from Slight Impairment to High Average) and Cognitive Flexibility (from Slight to Average Impairment).

Discussion

The combination treatment with lacosamide and oxcarbazepine showed superior results over lacosamide monotherapy in treating different ADHD indicators. The superior results of the combination treatment were obtained despite the dose of lacosamide being substantial lower in combination treatment than in monotherapy.

Neurovegetative functions as much as neuropsychological sensations, intellectual yield, pedagogical evolution and social interaction were significantly improved under the lacosamide and oxcarbazepine combination therapy, going beyond what was observed during the lacosamide monotherapy.

The improvement after administration of lacosamide and oxcarbazepine was gradual and maintainable. This is in contrast to the sudden improvements that appear after administration of molecular stimulants such as methylphenidate, risperidone and benzodiazepines, and which are short-lasting. This supports the hypothesis that the type of mechanism of action of lacosamide and oxcarbazepine is intracellular—contrary to the effects of molecular stimulators acting within the intersynaptic space.

Since the type of action of lacosamide and oxcarbazepine involves an intracellular mechanism, it is very likely that the pro-longed administration of these two molecules will continue to produce an improvement in ADHD symptoms.

The approach discussed in this study differs from various approaches of the same nature in which the authors or inventors relied on pro-serotonergic or other stimulant/low-dose effects that are obtained when small doses of antiepileptic drugs are administered to a patient. In this study, the doses used are within the known clinical range.

Example 2—Combination of Lacosamide and Oxcarbazepine in Treating Autism

A 21-year old patient suffering from autism was treated with the combination of lacosamide and oxcarbazepine for a period of 9 weeks.

The patient has not been undergoing a lacosamide and/or oxcarbazepine monotherapy prior to the administration of the combination treatment as part of this study.

Materials and Methods

The patient was evaluated neuropsychologically before and after the administration of the treatment. The pre- and post-treatment results were compared. The tests included:

1. Non Verbal Intelligence Test (TONI-4)
2. Conners' Continuous Performance Test (CPT-II)
3. Wisconsin Cards Sorting Test (WCST)
4. Trail Making Test (TMT)
5. Digit Symbol Substitution Test (DIGIT-SYM)
6. Stroop Colours and Words Test
7. Controlled Oral Association Test
8. Rey-Osterrieth Auditory Verbal Learning Test
9. Rey-Osterrieth Complex Figure Test (ROXCARBAZEPINEF)
10. Test Purdue Pegboard The Tutor or closest family member was interviewed by the end of the study for a "Before-After" evaluation towards the end of the testing frame.

The patient was seen and evaluated by a psychologist and a medical doctor once a week for 9 weeks, establishing a canvas of his progression under treatment.

A therapy of lacosamide+oxcarbazepine was established, with doses being adjusted according to the clinical presentation of the patient. The two drugs were started together.

Treatment

The patient received oxcarbazepine at 600 mg/24 hs together with lacosamide at a dose of 100 mg/24 hs. The doses were progressively revised following a clinical evaluation with an interval of 7 days between each adaptation. Each of the molecules was dosed independently (if one was modified, the other was not modified before having verified 7 days of administration).

Results

Patient's Initial Clinical Review Before Treatment

The 21-year old patient was diagnosed with autism when he was a child (4 to 6 years old). The patient presented several large incapacities (social, cognitive). EEG and IRM were completely normal.

The patient previously received medication (neuroleptic treatment), prescribed (by psychiatrist) in order to attempt to mild his anger episodes. He was taking no medication in the course of this study, other than lacosamide and oxcarbazepine.

In presentation, the patient showed combined symptoms of autism and intellectual disability. However, in the tests that were carried out before the study, it was shown that his IQ is around 99 points, which is within the average for a subject of his age.

The patient did not present stereotyped movements or flapping—he has relatively developed motor skills (slow movements and fragile chain of gestures).

His mental activity was quite ordered but filled with anxious thoughts (around 6/10 were negative), fixed images, and a dysphasic condition. He also presented dysphemia and had a strong urge to repeat certain words out loud over and over again.

The patient did not witness fatigue or lethargic symptoms—although his mother said he can lack energy to finish many activities he is invited to participate in. The patient was hyperemotional.

The symptom that most disturbed him is anger that he cannot contain. He is also subject to mood instability, with over-exaggerated reactions to minor events, reactions of anger and almost insurmountable anxiety; also intermittent restlessness. The impulsive nature of these phenomena is evident.

He also presented kinesthetic hallucinations (presences, scopic, olfactory)

He had difficulties in interpersonal relationships, with a certain immaturity in reciprocity—a manifest but relative difficulty in maintaining and understanding the codes, which is especially visible outside his family environment. Presents very limited and dysfunctional expressiveness in normal conversation.

He witnessed a very light sleeping activity, with the sensation of controlling his dreams as thoughts. He can listen to whatever happens around him through the night. He had great difficulty in falling asleep—feeling physically tense. He wakes up tired.

Clinical Evolution Under Treatment

The improvement under the administration of lacosamide+oxcarbazepine therapy was gradual, without creating physical fatigue.

The patient's adaptation to language and reality were evident for the patient himself, for the tutor and for the consultants from the beginning of the study. The sense of progressive order won over his thoughts as much as the impression of a more important concentration skill.

The sleep induction was improved, the quality of mood that accompanies waking-up as well. By increasing the doses, the parameters of clarity in the social exchange were progressively more evident and the patient recovered more energy and willpower.

The impulsivity decreased markedly over the 9 weeks of testing, following treatment's progression in dosage.

The improvement of 4 parameters: Course of Thoughts, Sleep quality, the stability of his Mood and his Alterity or social interaction was substantial.

The highest effective dose in the combination therapy was the dose of oxcarbazepine 1200 mg/day+lacosamide 200 mg/day. At this dose, the positive effect on autism symptoms was gradually consolidating and stabilizing.

At 60 days of treatment the patient described himself as feeling "very well" overall.

Regarding his "capacity for dialogue" and the quality of his expression, his assessment was "Excellent". The ability to understand language when the patient was addressed was "much better." When he interacted with people, he felt that he was "doing well" and he did it easier and more regularly than before.

He realised that he is currently in a good mood and that he was previously in a "bad mood". The quality of his oral expression is unquestionably more stable and fluid; although a certain mannerism persists. The dysphemia has disappeared. The patient said he sleeps very well (induction, sleep quality, length and morning wake up quality).

The administration of lacosamide and oxcarbazepine combined therapy had a clinical benefit not only on what the patient identified as his mood disorder and heteroaggressiveness, but also on:

- the cognitive function:
  - improvement in his speaking
  - increased ability to concentrate
  - favourable modulation of understanding of what is said and heard (meaning)
- the quality of sleep; and
- the social approach.

These clinical elements, which were decisive in the definition of his diagnosis, are constitutive elements of the principle of Autism Spectrum Disorder.

Neuropsychological Evaluation

After 2 months of treatment with lacosamide and oxcarbazepine, the patient was tested with the same neuropsycholigcal tests as at the start of the study.

The comparative results are summarized in Table 6.

TABLE 6

Neuropsychological evaluation results for autism patient.

| Test | Evaluated Function | Involved Brain Structure | Severity Range October 2020 | October 2020 Level | Severity Range December 2020 | December 2020 Level |
|---|---|---|---|---|---|---|
| TONI-4 | Nonverbal Reasoning Ability | Frontal Lobe | IQ-99 | Average | IQ-103 | Average |
| CPT-2-c | Impulse Control | Frontal Lobe | 4 | Severe Deterioration | 3 | Mild Deterioration |
| CPT-2-o | Visual Attentional Ability | Frontal Lobe | 99.90% Clinical (6 inattention indicators. Fast but erratic). 98.57% probability of neurological alterations | Severe Deterioration | 92.15% Clinical (3 Inattention Indicators. Fast but erratic). None indicators within limitations in surveillance. 50% probability of neurological alterations. | Severe Deterioration |
| WCST | Reasoning (Abstraction Categorization) | Frontal Lobe | 3 | Mild Deterioration | 1 | Average |
| WCST | Cognitive flexibility | Frontal Lobe | 2 | Mild Deterioration | 1 | Average |
| TMT-A | Visual Tracking | Frontal Lobe | 0 | High Average | 0 | High Average |
| TMT-B | Resistance to Perseveration | Frontal Lobe | 0 | High Average | 0 | High Average |
| Digit-Symbol | Foxcarbazepineus and execute | Frontal Lobe | 2 | Light Deterioration | 2 | Light Deterioration |
| COWAT | Verbal fluency | Left Frontal Lobe | 4 | Severe Deterioration | 4 | Severe Deterioration |
| TAAVR-I | Attentional Hearing Ability | Left Hem | 2 | Mild Deterioration | 1 | Average |
| TAAVR-V | Immediate auditory-verbal retention | Left Hem | 0 | High Average | 1 | Average |
| TAAVR-D | Dilated auditory-verbal retention | Left Temp Hem | 0 | High Average | 0 | High Average |
| Stroop-p | Nominative capacity | Left Hem | 2 | Mild Deterioration | 2 | Mild Deterioration |
| Stroop-c | Nominative capacity | Right Hem | 2 | Mild Deterioration | 2 | Mild Deterioration |
| Stroop-c/p | Resistance to Perseveration | Frontal Lobe | 1 | Average | 1 | Average |
| TDFCR-c | Visual-motor coordination | Right Parietal Lobe | 1 | Average | 0 | High Average |
| TDFCR-m | Visual retention | Right Temp Lobe | 1 | Average | 0 | High Average |
| Fine motor agility | Dominant | Left Hem Pegs-d | 3 | Mild Deterioration | 2 | Light Deterioration |
| Fine motor agility | Non-dominant | Right Hem Pegs-nd | 3 | Mild Deterioration | 2 | Light Deterioration |

The independent Neuropsychology centre that conducted the tests concluded:

"The patient shows significant progress in executive functions mediated by the prefrontal portions of his cerebral cortex. This progress is materialized in the following indicators:

His level of self-control (inhibitory control) improved objectively. It is still within a clinical level, but less severe than before.

His attentional capacity improved significantly and although he is still at a clinical level, out of 6 inattention indicators that he initially presented, he currently only presents 3 inattention indicators. This suggests that there has been progress in restoring attentional function.

He has gone from being a clinically inattentive person to being a person without diagnostic criteria for inattention but with some indicators that point more towards impulsivity (therefore he still fails in activities that require sustained attention). His reasoning capacity (abstraction) went from clinical levels to normal levels, which suggests that he now has the ability to better organize his thoughts and make sense of his experiences, thereby better organizing his behavior.

It improved slightly in indicators such as motor agility, visual-motor coordination, visual retention, cognitive flexibility, which suggests that in 3 more months of treatment we could see a substantial improvement in these indicators.

Some indicators still do not respond and have remained at clinical levels, such as verbal fluency and planning."

These results confirm the observations made throughout the clinical evaluation.

It should be noted that this improvement was obtained without any type of therapeutic, academic or supplementary medication monitoring.

Discussion

A combination of lacosamide and oxcarbazepine is very effective in treating a broad range of autism symptoms. The improvement of autism symptoms is gradual and long-lasting upon continued administration of the combination therapy.

This study shows that not only the combination of lacosamide and oxcarbazepine allows to achieve control of neurophysiological aspects (quality of sleep, lack of daytime energy, motor skills), but also to modulate the psychic expression of the neurological trouble (anxiety, concentration, capacity to compress/expression, relationship with language and therefore with reality), achieving an integration such that the quality of the patient's life is enhanced (cognitive, physiological, psychological and social), reaching levels of comfort and satisfaction that were non-existent before the treatment.

The combination of lacosamide and oxcarbazepine is clearly a very powerful solution for patients suffering from executive function disorders, such as autism.

Example 3—Combination of Lacosamide and Oxcarbazepine in Treating Executive Function Disorder The combination of lacosamide and oxcarbazepine has been administered to three additional patients with various symptoms associated with executive function disorder. The combination of lacosamide and oxcarbazepine was successful in alleviating different symptoms of executive function disorder. The results are demonstrated in Tables 7-9.

TABLE 7

| Case study A: Male, 15 years old. | |
|---|---|
| Conditions/symptoms the subject was diagnosed with: | Severe ADHD, hyperkinesia, working memory perturbed, impulsivity, very low concentration, major academic difficulties, insomnia, mood disorder, severe tiredness, anhedonia |
| Drugs the subject received prior to therapy used in this study | Valproic Acid<br>Methylphenidate<br>Lamotrigine<br>None showed lasting improvement in treating subject's symptoms |
| Therapy used in this study | Oxcarbazepine + Lacosamide |
| Dosage used: | Oxcarbazepine 600 mg every 12 hours (or 1,200 mg/day)<br>Lacosamide 100 mg every 12 hours (or 200 mg/day) |
| Period of administration: | 11 months |
| Observations/ Conclusions | Resolution of impulsivity, insomnia, hyperkinesia, and mood symptoms. Resolution of lethargic condition. Memory became slowly more and more performant.<br>Results highly improved in academic and pedagogic environment (he became not only able to pay attention through a long period of time, but also to organize and realize his work independently)<br>Neurophysiological and Neuropsychological symptoms were alleviated or resolved by the application of the lacosamide and oxcarbazepine combined therapy. This was not accomplished by administration of other mood-influencing drugs such as lamotrigine alone (or in combination with methylphenidate).<br>No adverse secondary effects were created by the administration of the combination therapy (unlike the adverse effects observed in ADHD patients receiving regular ADHD treatment, for example, Methylphenidate).<br>Combination of lacosamide and oxcarbazepine improved various symptoms of executive function disorder. |

TABLE 8

| Case Study B: Male, 42 years old. | |
|---|---|
| Conditions/symptoms the subject was diagnosed with: | Severe ADHD, hyperkinesia, overabundant thoughts, tachypsichia, major difficulty with concentration, impulsiveness, insomnia, dysphoria |
| Drugs the subject received prior to therapy used in this study | No previous treatment |
| Therapy used in this study | Oxcarbazepine + Lacosamide |
| Dosage used: | Oxcarbazepine 600 mg every 12 hours (or 1,200 mg/day)<br>Lacosamide 100 mg every 12 hours (or 200 mg/day) |
| Period of administration: | 6 months |
| Observations/ Conclusions | Resolution of impulsivity, insomnia, hyperkinesia, and mood symptoms.<br>Consciousness invasive thoughts and disordered activity smoothed and disappeared.<br>Neurophysiological and Neuropsychological symptoms were alleviated or resolved by the application of the lacosamide and oxcarbazepine combined therapy. |

TABLE 9

| Case Study C: Male, 13 years old. | |
|---|---|
| Conditions/symptoms the subject was diagnosed with: | Severe autism (Level 3), blindness, epilepsy, hyperkinesia, auto-hetero-aggressive behaviors, motor (flapping, arching) - vocal - objectual stereotypies, impulsiveness, insomnia, dysphoria |
| Drugs the subject received prior to therapy used in this study | Levetiracetam<br>Valproic Acid<br>Carbamazepine<br>Risperidone<br>Clonazepam |
| Therapy used in this study | Oxcarbazepine alone<br>then<br>Oxcarbazepine + Lacosamide |
| Dosage used: | Oxcarbazepine 300 mg every 12 hours (or 600 mg/day)<br>Lacosamide 100 mg every 12 hours (or 200 mg/day) |

TABLE 9-continued

| Case Study C: Male, 13 years old. | |
|---|---|
| Period of administration: | 9 months |
| Observations/ Conclusions | Oxcarbazepine alone<br>Minor improvement to subject's hyperkinesia and impulsiveness. However, instability remained in sleeping pattern (length of nights, mood at waking up, interruptions in the night and following insomnia). In addition, the subject did not approve in the way he behaved during awake moments, the quality of his day's attention. He maintained aggressive behavior and lack of interactivity with other members of the household.<br>Oxcarbazepine + Lacosamide<br>Autism regressed to stage 2 (interaction became possible, performing tasks, the subject become interested in different activities).<br>Resolution of aggressiveness, insomnia, hyperkinesia, and dysphoric symptoms. Stereotypies reduced and softened its expression. Sleep became regular and continuous.<br>Neurophysiological and Neuropsychological symptoms were alleviated or resolved by the application of the lacosamide and oxcarbazepine combined therapy. Importantly, all other psychoactive treatments have been abandoned. Thus, the subject's improvement is attributed solely to the combination therapy of lacosamide and oxcarbazepine. Oxcarbazepine alone was not sufficient to deliver the desired therapeutic result. |

The invention claimed is:

1. A method of treating an executive function disorder comprising administering (a) lacosamide; and (b) oxcarbazepine, to a subject in need thereof, wherein the lacosamide is administered to the subject in an amount of at least 100 mg/day and the oxcarbazepine is administered to the subject in an amount of at least 600 mg/day, wherein the amount of oxcarbazepine administered to the subject is:
(i) 1200 mg/day or less when the subject weighs less than 50 kg; or
(ii) 2400 mg/day or less when the subject weighs 50 kg or more.

2. The method of claim 1, wherein the executive function disorder is associated with attention deficit hyperactivity disorder (ADHD), or autism.

3. The method of claim 1, wherein the lacosamide and the oxcarbazepine are administered to the subject simultaneously, separately or sequentially.

4. The method of claim 1, wherein:
(a) the lacosamide is administered per the following treatment regimen:
(i) an initial amount of 100 mg/day, which if tolerated by the patient is followed by:
(ii) every 1-2 weeks increasing the amount by 50-100 mg up to a maximum amount in the range 200-500 mg/day and maintaining the daily amount thereat; and
(b) the oxcarbazepine is administered per the following treatment regimen:
(i) an initial amount of 600-750 mg/day, which if tolerated by the patient is followed by:
(ii) after 6-7 weeks increasing the amount to the amount in the range 750-1800 mg/day and maintaining the daily amount thereat.

5. The method of claim 1, wherein:
(a) the lacosamide is administered per the following treatment regimen:
(i) an initial amount of 100 mg/day, which if tolerated by the patient is followed by:
(ii) every week increasing the amount by 50-100 mg up to a maximum amount in the range 200-400 mg/day and maintaining the daily amount thereat; and
(b) the oxcarbazepine is administered per the following treatment regimen:
(i) an initial amount of 600 mg/day, which if tolerated by the patient is followed by:
(ii) after 6-7 weeks increasing the amount to the amount in the range 900-1200 mg/day and maintaining the daily amount thereat.

6. The method of claim 1, wherein the oxcarbazepine is administered per the following treatment regimen:
(i) 600 mg/day for 6-7 weeks, followed by:
(ii) 900 mg/day and maintaining the daily amount thereat, and
(iii) optionally, after 1-4 weeks:
i. increasing the oxcarbazepine to 1200 mg/day and maintaining the daily amount thereat; or
ii. decreasing the oxcarbazepine to 600 mg/day and maintaining the daily amount thereat.

7. The method of claim 1, wherein:
(a) the lacosamide is administered per the following treatment regimen:
(i) an initial amount of 100 mg/day, which if tolerated by the patient is followed by:
(ii) every 1-2 weeks increasing the amount by 50-100 mg up to a maximum amount in the range 200-500 mg/day and maintaining the daily amount thereat; and
(b) the oxcarbazepine is administered per the following treatment regimen:
(i) an initial amount of 600-750 mg/day, which if tolerated by the patient is optionally followed by:
(ii) every week increasing the amount by 150-300 mg to the amount in the range 900-2400 mg/day and maintaining the daily amount thereat.

8. The method of claim 1, wherein:
(a) the lacosamide is administered per the following treatment regimen:
(i) an initial amount of 100 mg/day, which if tolerated by the patient is followed by:
(ii) every week increasing the amount by 50-100 mg up to a maximum amount in the range 200-400 mg/day and maintaining the daily amount thereat; and
(b) the oxcarbazepine is administered per the following treatment regimen:
(i) an initial amount of 600 mg/day, which if tolerated by the patient is optionally followed by:
(ii) every week increasing the amount by 300 mg up to a maximum amount of 1200 mg/day and maintaining the daily amount thereat.

9. The method of claim 1, wherein the lacosamide is administered per the following treatment regimen:
(i) 100 mg/day for 1-2 weeks, followed by:
(ii) 200 mg/day and maintaining the daily amount thereat, optionally, after 1-2 weeks, followed by:
(iii) 300 mg/day for 1-2 weeks, optionally followed by:
(iv) 400 mg/day and maintaining the daily amount thereat.

10. The method of claim 1, wherein the oxcarbazepine is administered per the following treatment regimen:
(i) 600 mg/day for 1-2 weeks, followed by:
(ii) 900 mg/day for 1-2 weeks, followed by:

(iii) 1200 mg/day and maintaining the daily amount thereat, (iv) optionally, after 1-2 weeks at 1200 mg/day increasing the oxcarbazepine to 1800 mg/day and maintaining the daily amount thereat, or (v) optionally, after 1-2 weeks at 1800 mg/day increasing the oxcarbazepine to 2400 mg/day and maintaining the daily amount thereat.

11. The method of claim 1, wherein the executive function disorder is characterized by or associated with one or more symptoms selected from:

(i) hyperactivity and/or impulsivity;
(ii) involuntary enuresis;
(iii) aggressive behaviour;
(iv) insomnia or hypersomnia;
(v) impaired attention processing;
(vi) impaired communication;
(vii) impaired social skills;
(viii) impaired visual and/or auditory processing;
(ix) anhedonia;
(x) tachypsichia;
(xi) dysphoria; and
(xii) stereotypies.

12. The method of claim 1, wherein the treatment alleviates one or more symptoms of the executive function disorder selected from:

(i) hyperactivity and/or impulsivity;
(ii) involuntary enuresis;
(iii) aggressive behaviour;
(iv) insomnia or hypersomnia;
(v) impaired attention processing;
(vi) impaired communication;
(vii) impaired social skills;
(viii) impaired visual and/or auditory processing;
(ix) anhedonia;
(x) tachypsichia;
(xi) dysphoria; and
(xii) stereotypies.

13. The method of claim 1, wherein the lacosamide and the oxcarbazepine are each administered in 1-3 doses per day.

14. The method of claim 1, wherein the lacosamide and the oxcarbazepine are each administered in 2 doses per day.

15. The method of claim 1, wherein the lacosamide and the oxcarbazepine are co-formulated in a single pharmaceutical composition.

16. The method of claim 1, wherein lacosamide and oxcarbazepine are both present as separate pharmaceutical compositions in a kit.

17. The method of claim 1, wherein the amount of lacosamide administered to the subject is 400 mg/day or less.

18. The method of claim 1, wherein the amount of lacosamide administered to the subject is 200 mg/day and the amount of oxcarbazepine administered to the subject is between 600-1200 mg/day.

* * * * *